United States Patent
Lee et al.

(10) Patent No.: US 9,150,782 B2
(45) Date of Patent: Oct. 6, 2015

(54) FLUORESCENT TRACER FOR WATER-SOLUBLE FILMS, RELATED METHODS, AND RELATED ARTICLES

(71) Applicant: MONOSOL, LLC, Merrillville, IN (US)

(72) Inventors: David M. Lee, Crown Point, IN (US); Stephen Bullock, Chicago, IL (US); Nicholas Zeese, Michigan City, IN (US)

(73) Assignee: MONOSOL, LLC, Merrillville, IN (US)

(*) Notice: Subject to any disclaimer, the term of this patent is extended or adjusted under 35 U.S.C. 154(b) by 0 days.

(21) Appl. No.: 14/562,148

(22) Filed: Dec. 5, 2014

(65) Prior Publication Data

US 2015/0159082 A1 Jun. 11, 2015

Related U.S. Application Data

(60) Provisional application No. 61/912,689, filed on Dec. 6, 2013.

(51) Int. Cl.
*G01N 21/64* (2006.01)
*C09K 11/02* (2006.01)
(Continued)

(52) U.S. Cl.
CPC ............. *C09K 11/025* (2013.01); *C09K 11/06* (2013.01); *C11D 3/0005* (2013.01); *C11D 3/2096* (2013.01); *C11D 3/3418* (2013.01);
(Continued)

(58) Field of Classification Search
CPC .................... G01N 2021/6441; G01N 33/582; G01N 33/58
See application file for complete search history.

(56) References Cited

U.S. PATENT DOCUMENTS 2,220,099 A 11/1940 Guenther et al.
2,477,383 A 7/1949 Lewis
(Continued)

FOREIGN PATENT DOCUMENTS

EP 0 197 434 A2 10/1986
EP 0791680 A2 8/1997
(Continued)

OTHER PUBLICATIONS

Dye Tracing, Wikipedia Entry, downloaded from the Internet at <http://en.wikipedia.org/wiki/Dye_tracing> (page last modifed Apr. 26, 2014).
(Continued)

*Primary Examiner* — Kiho Kim
(74) *Attorney, Agent, or Firm* — Marshall, Gerstein & Borun LLP

(57) ABSTRACT

Disclosed herein are fluorescent tracer compositions and water-soluble polymer compositions containing fluorescent compounds for tracing one or more components in the polymer compositions. More particularly, the disclosure relates to fluorescent tracer compositions including a fluorophore and a bitterant aversive component to be incorporated into a water-soluble polymer composition such as a water-soluble film. An aversive compound such as a bitterant is desirably incorporated into the polymer composition as a deterrent to ingestion of the polymer composition (or an article made therefrom). Qualitative or quantitative detection of the fluorophore in the polymer composition can be correlated to a qualitative or quantitative detection of a corresponding traced material in the polymer composition, for example the bitterant aversive component. Related articles and methods for making and using the polymer compositions are also disclosed.

38 Claims, 3 Drawing Sheets

(51) Int. Cl.

| | | |
|---|---|---|
| *C09K 11/06* | (2006.01) | |
| *C11D 3/42* | (2006.01) | |
| *C11D 3/00* | (2006.01) | |
| *C11D 3/37* | (2006.01) | |
| *C11D 3/20* | (2006.01) | |
| *C11D 3/34* | (2006.01) | |

(52) U.S. Cl.
CPC ............... *C11D3/3753* (2013.01); *C11D 3/42* (2013.01); *G01N 21/6428* (2013.01); *C09K 2211/1007* (2013.01); *C09K 2211/1088* (2013.01); *G01N 2021/6439* (2013.01)

(56) References Cited

U.S. PATENT DOCUMENTS

| | | |
|---|---|---|
| 3,664,961 A | 5/1972 | Norris |
| 3,919,678 A | 11/1975 | Penfold |
| 4,000,093 A | 12/1976 | Nicol et al. |
| 4,222,905 A | 9/1980 | Cockrell, Jr. |
| 4,239,659 A | 12/1980 | Murphy |
| 4,246,612 A | 1/1981 | Berry et al. |
| 4,810,410 A | 3/1989 | Diakun et al. |
| 5,114,611 A | 5/1992 | Van Kralingen et al. |
| 5,137,646 A | 8/1992 | Schmidt et al. |
| 5,227,084 A | 7/1993 | Martens et al. |
| 5,576,281 A | 11/1996 | Bunch et al. |
| 5,783,541 A | 7/1998 | Tack et al. |
| 6,468,554 B1 | 10/2002 | Ichino |
| 6,599,871 B2 | 7/2003 | Smith |
| 2002/0033004 A1 | 3/2002 | Edwards et al. |
| 2003/0060387 A1 | 3/2003 | Hsu et al. |
| 2003/0060390 A1 | 3/2003 | Demeyere et al. |
| 2003/0126282 A1 | 7/2003 | Sarkar et al. |
| 2003/0139312 A1 | 7/2003 | Caswell et al. |
| 2004/0204337 A1 | 10/2004 | Corona et al. |
| 2005/0101507 A1 | 5/2005 | Jaynes |
| 2005/0123935 A1* | 6/2005 | Haugland et al. ................ 435/6 |
| 2007/0219111 A1 | 9/2007 | Ward et al. |
| 2010/0025619 A1* | 2/2010 | Riva et al. ........................ 252/67 |
| 2010/0175845 A1 | 7/2010 | Gauto et al. |
| 2011/0023240 A1 | 2/2011 | Fossum et al. |
| 2011/0189413 A1 | 8/2011 | Denome et al. |
| 2013/0108555 A1 | 5/2013 | Lary, Jr. et al. |
| 2014/0199460 A1 | 7/2014 | Lee et al. |

FOREIGN PATENT DOCUMENTS

| | | |
|---|---|---|
| EP | 1375637 A1 | 1/2004 |
| EP | 2196531 A1 | 6/2010 |
| EP | 2258820 A1 | 12/2010 |
| GB | 1 137 741 A | 12/1968 |
| WO | WO-96/08555 A1 | 3/1996 |
| WO | WO-2014/026855 A1 | 2/2014 |
| WO | WO-2014/026856 A1 | 2/2014 |

OTHER PUBLICATIONS

International Search Report and Written Opinion, International Application No. PCT/US2014/068848, mailed Mar. 5, 2015.

Suo et al., Poly (vinyl alcohol) thin film filled with CdSe—ZnS quantum dots: fabrication, characterization and optical properties, Mater. Chem. Phys., 119:237-42 (2010).

Final Report: Study of Aversive Agents, U.S. Consumer Product Safety Commission (Nov. 18, 1992).

* cited by examiner

FLUORESCENT TRACER FOR WATER-SOLUBLE FILMS, RELATED METHODS, AND RELATED ARTICLES

FIELD OF THE DISCLOSURE

The present disclosure relates generally to fluorescent tracer compositions and to water-soluble polymer compositions containing fluorescent compounds for tracing one or more components therein. More particularly, the disclosure relates to fluorescent tracer compositions including a fluorophore and a bitterant aversive component to be incorporated into a water-soluble polymer composition such as a water-soluble film.

BACKGROUND

Water-soluble polymeric compositions such as films include a variety of components such as water-soluble polymers (e.g., polyvinyl alcohol (PVOH)), plasticizers, and various other additives. Such compositions are commonly used as packaging materials to simplify dispersing, pouring, dissolving and dosing of a material to be delivered. For example, packets made from water-soluble film are commonly used to package household care compositions, e.g., as a pouch containing a laundry or dish detergent. A consumer can directly add the pouch to a mixing vessel, such as a bucket, sink or washing machine. Advantageously, this provides for accurate dosing while eliminating the need for the consumer to measure the composition. The pouch may also reduce mess that would be associated with dispensing a similar composition from a vessel, such as pouring a liquid laundry detergent from a bottle. The pouch also insulates the composition therein from contact with the user's hands. In sum, soluble polymeric film packets containing pre-measured agents provide for convenience of consumer use in a variety of applications.

It can be difficult to qualitatively detect or quantitatively measure various components of water-soluble polymeric compositions, in particular after formed into a solid material such as a film. Such compositions can be difficult to analyze using analytical tools such as HPLC (high-pressure liquid chromatography) and GPC (gel-permeation chromatography), so the separation and analysis of their components must be accomplished with more labor intensive methods. Complex separation methods such as soxhlet extraction prior to quantitative analysis can be possible; however such a process is time-consuming and impractical, in particular for rapid quality testing at the industrial scale.

There remains a need for improved qualitative and quantitative analytical detection techniques for water-soluble polymer composition components, in particular where it is important for safety or performance reasons to validate that a specific component is qualitatively present and/or quantitatively incorporated at a desired concentration in the composition.

SUMMARY

The present disclosure relates generally to fluorescent tracer compositions and to water-soluble polymer compositions containing fluorescent compounds for tracing one or more components in the polymer compositions. More particularly, in one embodiment the disclosure relates to fluorescent tracer compositions including a fluorophore and a bitterant aversive component to be incorporated into a water-soluble polymer composition such as a water-soluble film. An aversive compound such as a bitterant is desirably incorporated into the polymer composition as a deterrent to ingestion of the polymer composition (or an article made therefrom) by a child or animal. Qualitative or quantitative detection of the fluorophore in the polymer composition can be correlated to a qualitative or quantitative detection of a corresponding traced material in the polymer composition, for example the bitterant aversive component.

The disclosed compositions and methods address the issues noted above for detection and quantitation of one or more components (e.g., a bitterant) in a water-soluble polymer composition, e.g. for quality assurance purposes, for example when such components are not measurable using standard analytical tools. The disclosed compositions and methods solve this problem by incorporating a fluorophore as a tracer for the material to be detected or quantitated. The fluorophore is incorporated at a level that can be detected and/or measured accurately and easily by various optical methods (e.g., visual observation by a human, or spectrophotometric determination). When the fluorophore and the traced material are incorporated at a known ratio, quantitative detection and measurement of the fluorophore can be correlated to quantitative detection and measurement the traced material.

Unsuccessful past attempts by the present inventors included the incorporation of various ultraviolet (UV) absorbers into a PVOH solution as a tracer for a target material. It was thought that the UV absorptivity of the PVOH solution could be measured by a UV-Vis spectrometer to detect the target materials. The method proved to be unsuccessful, however, as the PVOH solution itself was absorptive to UV light, and the necessary levels of incorporation of the tracer UV absorber were too high to be practical. Additionally, the sensitivity to changes in tracer UV absorber concentration was too low, requiring concentration changes of greater than 10% to be measurable. This in turn led to the inability of reliably measuring changes in target material concentration of less than 10%, which is not precise enough for some applications.

Other attempts by present inventors for the particular application of tracing a denatonium bitterant in a water-soluble polymer composition included the use of water-soluble fluorophore tracers within the film formulations. These attempts were unsuccessful due to a chemical incompatibility between the denatonium benzoate bittering agent and the fluorophore tracer (a functionalized distyryl biphenyl made water-soluble with sulfonate groups). The incompatibility stemmed from an interaction between the cationic nature of denatonium and the anionic nature of the fluorophore. Specifically, the anionic sulfonate groups, which are added to many otherwise insoluble optical brightener fluorophores to imbue water solubility, reacted with the cationic portion of the denatonium to form an insoluble salt. The reaction is nearly instantaneous in some cases and results in a white precipitate. Most water-soluble optical brightener fluorophores utilize some form of anionic pendant group to imbue water solubility. Other optical brightener fluorophores that do not possess such pendent groups are either marginally water-soluble or rare or difficult to synthesize, and thus impractical and prohibitively expensive. Without some form of anionic functionalization, fluorophores are generally insoluble in water as they possess many conjugated rings which allow for strong UV light absorption, but the molecules in turn possess little polarity and are thus immiscible with water.

In one aspect, the present disclosure addresses the problems described above by providing a tracer composition including a water-insoluble fluorophore in combination with a water-soluble material to be traced by the fluorophore (e.g., a bitterant such as a denatonium bitterant). The fluorophore can be detected and measured easily within a solid polymer composition or an aqueous composition containing the same by way of fluorescence spectroscopy. The water-insoluble fluorophore (e.g., a non-reactive and/or a non-ionically functionalized fluorophore) can be homogeneously distributed throughout an aqueous composition as an emulsion with the aid of a suitable emulsifier. The emulsification allows the fluorophore to be added to an aqueous composition including the traced material (e.g., the denatonioum bitterant) and/or other water-soluble polymer composition components without reaction or other incompatibility (e.g., based on the absence of anionic fluorophores possibly reactive with cationic components thereof). Suitably, the fluorophore and the traced material are added to a polymer composition as a mixture of the fluorophore and the traced material and in a predetermined, known ratio between the fluorophore and the traced material. This ensures that the two materials are added simultaneously and at the desired ratio, thus permitting tracing and quantitative detection of the fluorophore to be correlated to a quantitative detection of the traced material.

Sample preparation for fluorophore detection is minimal and fast, which is ideal for rapid production quality testing and verification. In one embodiment, the water-soluble polymer composition, whether it is in the form of an aqueous solution (e.g., a casting solution), a solid part, or a film, is dissolved/diluted to a specified weight percent solids level using deionized water. The dilution factor used can, for example, depend on the fluorophore's concentration within the composition and the specific properties of the polymeric material being measured. In one embodiment, the sample will be dilute enough to reduce quenching of the emitted photons but concentrated enough to yield a sufficiently high photon count to be detectable by a spectrometer. Rapid and accurate spectrophotometric detection of the fluorophore and, correspondingly the traced material, is particularly desirable for a rapid quality monitoring system that ensures desired loading levels for materials traced by the fluorophore. In various embodiments, such rapid quality monitoring can be performed in-line (e.g., testing such as spectrophotometric testing directly in product production flow path) or offline (e.g., testing of a product sample removed from the production flow path at an intermediate or final location in same).

The disclosed compositions and methods can be designed to offer a high level of sensitivity, accuracy, and chemical compatibility. The approach allows for the concentration of the fluorophore to be kept low so as to not increase cost or alter the appearance of the PVOH material in an undesirable fashion. This is an improvement over the use of UV absorbers as a tracer material, which exhibit low sensitivity when using transmission UV-Vis spectroscopy. This method is also much faster and easier than separation methods such as soxhlet extraction, which not only require a high level of training, but also a delicate testing apparatus which requires a large amount of time to effectively separate two materials. Beyond this, the use of a soxhlet extraction method or something similar would still require chemical analysis through the use of HPLC or GPC, both of which require a high level of training to perform and are subject to interactions with column packing materials that can further complicate and compromise analysis.

One aspect of the disclosure relates to a tracer composition including: an aqueous, homogeneous mixture including: a water-insoluble fluorophore having a first fluorescence emission spectrum including at least one characteristic emission wavelength when exposed to electromagnetic radiation including a characteristic excitation wavelength for the fluorophore, the fluorophore being homogeneously dispersed throughout the mixture, and a water-soluble material having a second fluorescence emission spectrum which is distinct from the first fluorescence emission spectrum when exposed to the same electromagnetic radiation including the characteristic excitation wavelength for the fluorophore, the water-soluble material being homogeneously mixed in solution throughout the mixture.

Another aspect of the disclosure relates to a tracer composition including: a homogeneous mixture including: a water-insoluble fluorophore having a first fluorescence emission spectrum including at least one characteristic emission wavelength when exposed to electromagnetic radiation including a characteristic excitation wavelength for the fluorophore, the fluorophore being homogeneously dispersed throughout the mixture, a water-soluble material having a second fluorescence emission spectrum which is distinct from the first fluorescence emission spectrum when exposed to the same electromagnetic radiation comprising the characteristic excitation wavelength for the fluorophore, the water-soluble material being homogeneously mixed in solution throughout the mixture, and at least one of water and a water-miscible solvent as a medium for the water-insoluble fluorophore and the water-soluble material.

Another aspect of the disclosure relates to a water-soluble polymer composition including: a solid mixture including: a water-soluble polymer, a fluorophore having a first fluorescence emission spectrum comprising at least one characteristic emission wavelength when exposed to electromagnetic radiation comprising a characteristic excitation wavelength for the fluorophore, the fluorophore being homogeneously distributed throughout the mixture, and a material having a second fluorescence emission spectrum which is distinct from the first fluorescence emission spectrum when exposed to the electromagnetic radiation including the characteristic excitation wavelength for the fluorophore, the material being homogeneously distributed throughout the mixture; wherein: when the water-soluble polymer composition is dissolved and mixed in water to form a dissolved composition, the fluorophore remains homogeneously distributed throughout the dissolved composition.

Another aspect of the disclosure relates to a plurality of water-soluble polymer compositions including: two or more water-soluble polymer compositions of any of the variously disclosed embodiments, wherein: each water-soluble polymer composition is different from each other water-soluble polymer composition in at least one aspect, and each water-soluble polymer composition includes the same fluorophore and the same traced material.

Another aspect of the disclosure relates to an article including: a water-soluble polymer composition of any of the variously disclosed embodiments in the form of a container defining an interior container volume; and a composition contained in the interior container volume.

Another aspect of the disclosure relates to a method for forming a water-soluble polymer composition, the method including: mixing a water-soluble polymer and a tracer composition of any of the variously disclosed embodiments to form a polymer-fluorophore-material blend; and forming the polymer-fluorophore-material blend into a solid water-soluble polymer composition, wherein the fluorophore and the material are homogeneously distributed throughout the water-soluble polymer composition.

Another aspect of the disclosure relates to a method for forming a water-soluble polymer composition, the method including: mixing a water-soluble polymer and a tracer composition to form a polymer-fluorophore-material blend, wherein the tracer composition includes a homogeneous mixture including: a fluorophore having a first fluorescence emission spectrum including at least one characteristic emission wavelength when exposed to electromagnetic radiation including a characteristic excitation wavelength for the fluorophore, the fluorophore being homogeneously distributed throughout the mixture, and a material having a second fluorescence emission spectrum which is distinct from the first fluorescence emission spectrum when exposed to the electromagnetic radiation including the characteristic excitation wavelength for the fluorophore, the material being homogeneously distributed throughout the mixture; and forming the polymer-fluorophore-material blend into a solid water-soluble polymer composition, wherein the fluorophore and the material are homogeneously distributed throughout the water-soluble polymer composition.

Another aspect of the disclosure relates to a method for detecting a fluorophore, the method including: providing a water-soluble polymer composition or according to any of the variously disclosed embodiments; exposing the composition or article to incident electromagnetic radiation including the characteristic excitation wavelength for the fluorophore; detecting for emitted electromagnetic radiation from the composition or article, the emitted electromagnetic radiation corresponding to the at least one characteristic emission wavelength of the fluorophore, wherein positive detection of the characteristic emission wavelength indicates that the material is present in the composition or article.

In a particular refinement of the various embodiments, the fluorophore is water-insoluble (e.g., and remains homogeneously dispersed throughout the tracer composition or dissolved water-soluble polymer composition); and the material is water-soluble (e.g., and remains homogeneously mixed in solution throughout the tracer composition or dissolved water-soluble polymer composition). In another refinement of the various embodiments, the fluorophore is water-soluble (e.g., and remains homogeneously mixed in solution throughout the tracer composition or dissolved water-soluble polymer composition); and the material is water-insoluble (e.g., and remains homogeneously dispersed throughout the tracer composition or dissolved water-soluble polymer composition). In another refinement of the various embodiments, the fluorophore and the material are water-soluble (e.g., and remain homogeneously mixed in solution throughout the tracer composition or dissolved water-soluble polymer composition). In another refinement of the various embodiments, the fluorophore and the material are water-insoluble (e.g., and remain homogeneously dispersed throughout the tracer composition or dissolved water-soluble polymer composition).

Further aspects and advantages will be apparent to those of ordinary skill in the art from a review of the following detailed description and accompanying drawings. While the compositions and methods are susceptible of embodiments in various forms, the description hereafter includes specific embodiments with the understanding that the disclosure is illustrative, and is not intended to limit the invention to the specific embodiments described herein.

DESCRIPTION OF THE DRAWINGS

The following detailed description of the various disclosed methods, processes, compositions, and articles refers to the accompanying drawings in which.

DETAILED DESCRIPTION

Figure 1A:
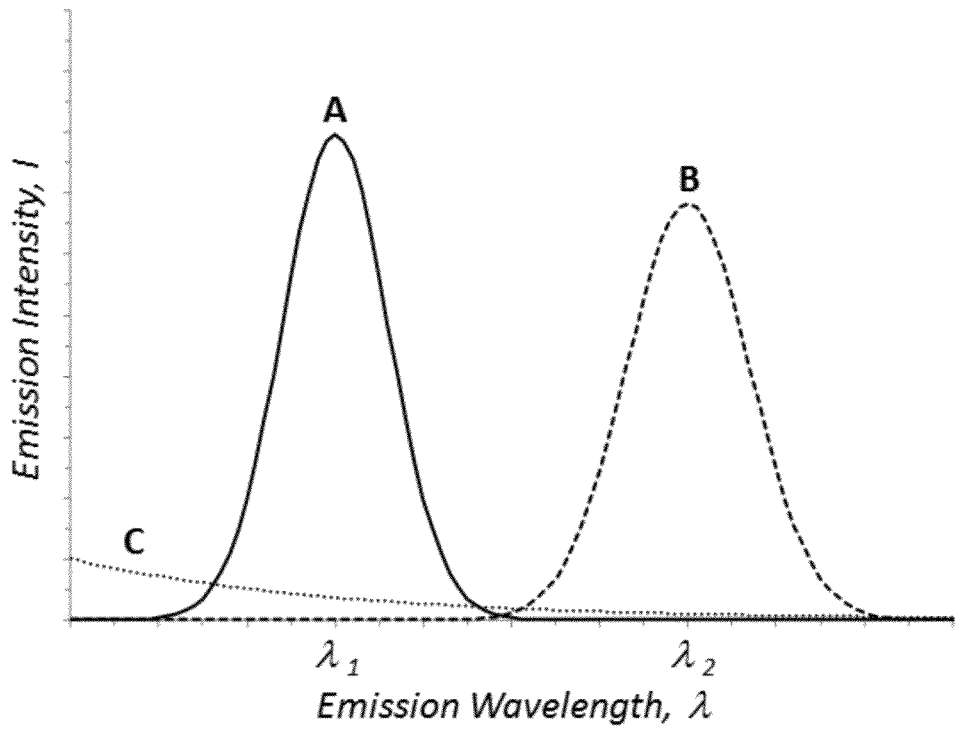
FIGS. 1A and 1B are graphs qualitatively illustrating examples of distinct fluorescence emission spectra for fluorophores and other water-soluble polymer composition components according to the disclosure.

Disclosed herein are fluorescent tracer compositions and water-soluble polymer compositions containing fluorescent compounds for tracing one or more components therein. More particularly, the disclosure relates to fluorescent tracer compositions including a fluorophore and a traced material such as bitterant aversive component to be incorporated into a water-soluble polymer composition (e.g., as a water-soluble film). As used herein, a "traced material" is a material that is added to and used in the variously disclosed compositions in combination with at least one fluorophore. By using a fluorophore and a traced material in tandem, the resulting correlation of the two components can be utilized such that qualitative or quantitative detection of the fluorophore in a composition (e.g., tracer composition, solid water-soluble polymer composition, dissolved water-soluble polymer composition) can be correlated to a qualitative or quantitative detection of the corresponding traced material in the composition. While the disclosure below generally describes mixtures of a fluorophore and a traced material, it is specifically contemplated that a single fluorophore can also be used as a tracer for more than one traced material in the same composition (e.g., tracer composition, water-soluble polymer composition, dissolved water-soluble polymer composition formed from same). In another embodiment, it is specifically contemplated that a plurality of fluorophores can be used to trace a plurality of traced materials in the same composition (e.g., tracer composition, water-soluble polymer composition, dissolved water-soluble polymer composition formed from same).

The tracer composition according to the disclosure is in the form of a homogeneous mixture which includes the fluorophore and the traced material homogeneously distributed throughout the mixture (e.g., in a liquid medium such as water and/or a water-miscible solvent). Suitably, the tracer composition is in the form of an aqueous homogeneous mixture of the fluorophore and the traced material. The fluorophore and the traced material have distinct fluorescence emission spectra to facilitate fluorescent detection of the fluorophore and correlation of the same with detection of the traced material.

The fluorophore and the traced material are homogeneously distributed throughout the tracer composition in any suitable manner, for example depending on the specific solubility characteristics of the fluorophore and the traced material. For example, the fluorophore and/or the traced material can be water-insoluble and remain homogeneously dispersed throughout the tracer composition (e.g., as a stable emulsion with the inclusion of an emulsifier). Similarly, the fluorophore and/or the traced material can be water-soluble and remain homogeneously mixed in solution throughout the tracer composition (e.g., as a dissolved component). Any particular combination of solubility traits can be selected that provides a stable, compatible mixture of the fluorophore and the traced material (e.g., they both remain homogeneously distributed throughout tracer composition without precipitation, settling, reaction, and/or phase separation, etc.). For instance, specific possible combinations include (i) a water-soluble fluorophore and a water-insoluble traced material, (ii) a water-insoluble fluorophore and a water-soluble traced material, (iii) a water-soluble fluorophore and a water-soluble traced material, and (iv) a water-insoluble fluorophore and a water-insoluble traced material (e.g., with the optional inclusion of one or more emulsifiers as desired for insoluble components).

As noted, the fluorophore and the traced material have distinct fluorescence emission spectra to facilitate fluorescent detection of the fluorophore (e.g., without undue interference from the traced material, which might have some level of fluorescent activity). More generally, the fluorophore has a fluorescence emission spectrum which is distinct from those of all other components of the tracer composition and/or the water-soluble polymer composition into which it is to be incorporated (e.g., where the other composition components might otherwise have some potentially interfering level of fluorescent activity). The fluorophore is generally characterized as having a first fluorescence emission spectrum with at least one characteristic emission wavelength when exposed to electromagnetic radiation at a characteristic excitation wavelength for the fluorophore. Similarly, the traced material is characterized as having a second fluorescence emission spectrum. The second fluorescence emission spectrum is distinct from the first fluorescence emission spectrum when exposed to electromagnetic radiation at the characteristic excitation wavelength for the fluorophore. Emission spectra can be distinct, for example, given a substantial emission intensity at a particular wavelength (e.g., a peak in the intensity vs. wavelength curve at the particular wavelength) in one spectrum (e.g., the fluorophore spectrum) as compared to the other spectrum (e.g., the traced material or non-fluorophore spectrum). In a limiting case, the traced material (or other composition component) is essentially non-fluorescent, either in general or at the excitation wavelength of the fluorophore, so the emission intensity vs. wavelength is essentially zero for the second fluorescence emission spectrum (i.e., which is thus distinct from a measurable first fluorescence emission spectrum signal). More generally, the traced material (or other composition component) might have some fluorescent activity. In this case, it is desirable that the fluorophore emission intensity at the fluorophore's characteristic emission wavelength is at least 2, 5, 10, 20, 50, or 100 or more times higher than the traced material emission intensity at the particular wavelength. Spectra also can be distinct based on different relative ratios between emission intensities at at least two different wavelengths, or more.

Figure 1B:
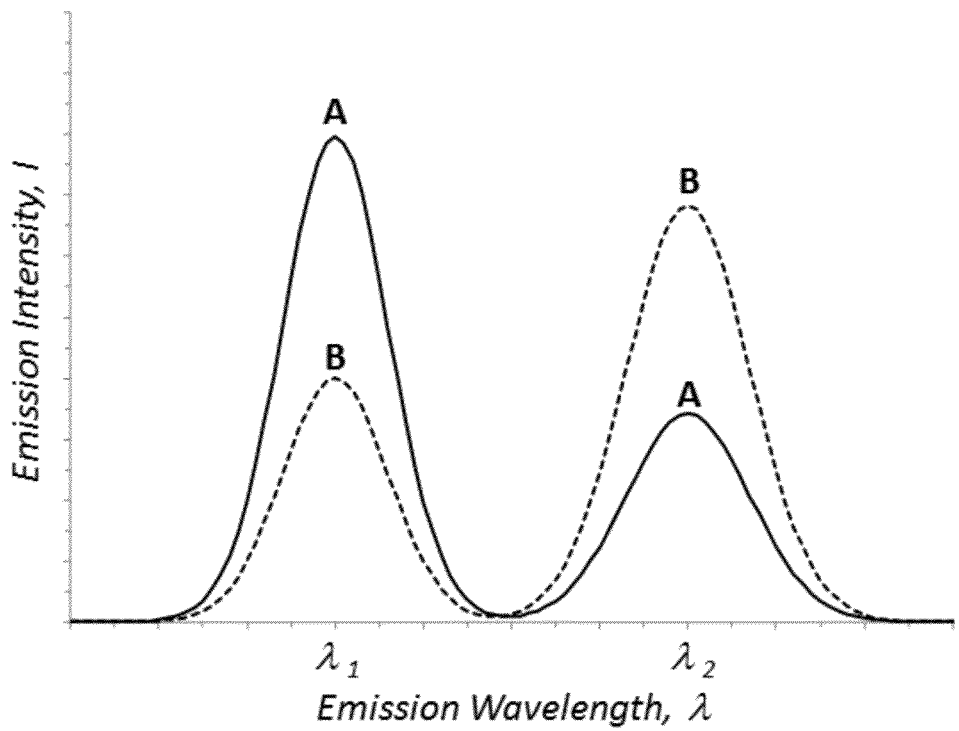

FIGS. 1A and 1B qualitatively illustrate different ways in which the first fluorescence emission spectrum A of the fluorophore can be distinct from the second fluorescence emission spectrum B or C of another material (e.g., traced material or other composition component). As illustrated in FIG. 1A, the fluorophore emission spectrum A has a characteristic (e.g., peak) emission intensity I at wavelength $\lambda_1$ (e.g., where $\lambda_1$ would be a suitable detection wavelength for fluorophore quantitation). Although emission spectrum B has a significant fluorescent emission at a different wavelength $\lambda_2$ (e.g., representing a different fluorophore tracing a different material or simply another (non-traced) composition component with substantial fluorescent emission), spectra A and B are distinct because spectrum B has essentially no emission intensity at the characteristic wavelength $\lambda_1$ for the fluorophore. Similarly, although emission spectrum C has some fluorescent emission at wavelength $\lambda_1$ (corresponding to the characteristic fluorophore peak), spectra A and C are distinct because spectrum C has a substantially lower emission intensity at the characteristic wavelength $\lambda_1$ for the fluorophore (e.g., as illustrated $I_A(\lambda_1)/I_C(\lambda_1)$ is about 16). As illustrated in FIG. 1B, the fluorophore emission spectrum A has two characteristic emission peaks at wavelengths $\lambda_1$ and $\lambda_2$ (e.g., where either of both of $\lambda_1$ and $\lambda_2$ would be a suitable detection wavelength for fluorophore quantitation). Although emission spectrum B has a significant fluorescent activity at wavelengths $\lambda_1$ and $\lambda_2$ (e.g., representing a different fluorophore tracing a different material), spectra A and B are distinct because the ratios of the two intensities are measurably distinct for each material (e.g., as illustrated $I_A(\lambda_1)/I_A(\lambda_2)$ is about 2.4 while $I_B(\lambda_1)/I_B(\lambda_2)$ is about 0.6).

The water-soluble polymer composition according to the disclosure can be in the form of a solid mixture (e.g., a film, pouch, or other form or article) which includes, among other common ingredients described below, a fluorophore and a traced material homogeneously distributed throughout the solid mixture. The fluorophore and the traced material have distinct fluorescence emission spectra as described above. When the water-soluble polymer composition is dissolved and mixed in water to form a dissolved composition, the fluorophore and the traced material remain homogeneously distributed throughout the dissolved composition. That is, similar to their behavior in the tracer composition, the fluorophore and the traced material form a stable, compatible mixture when the polymer composition is dissolved in water. This property is desirable so that the fluorophore can be reliably detected and quantitated in the dissolved composition, thus permitting a similar determination for the traced material. To this end, emulsifiers useful for inclusion in the tracer composition similarly can be incorporated into the polymer composition such that, upon dissolution, the emulsifier can stabilize a water-insoluble fluorophore and/or a water-insoluble traced material in the dissolved composition. The dissolved composition is suitably stirred or otherwise agitated upon initial formation to promote emulsification and composition homogeneity. If the dissolved composition is to be tested for the presence of the fluorophore by fluorescent emission, the composition can be re-stirred or re-agitated shortly prior to analysis to ensure composition homogeneity during analysis.

Figure 2:
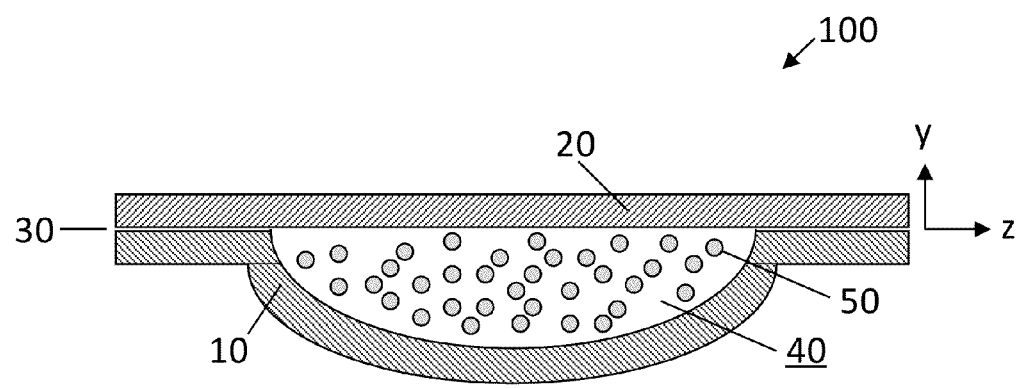
FIG. 2 is a side cross-sectional view of water-soluble pouch article for the delivery of a composition according to the disclosure.

The water-soluble polymer composition can be in the form of a container for storing and/or delivering a composition contained therein (e.g., delayed release of same, such as in a laundry or dishwashing aqueous wash medium). FIG. 2 illustrates such an article in which a water-soluble pouch 100 is formed from water-soluble polymer films 10, 20 sealed at an interface 30. One or both of the films 10, 20 include the fluorophore and the traced material homogeneously distributed therein. The films 10, 20 define an interior pouch container volume 40 which contains any desired composition 50 for release into an aqueous environment. The composition 50 is not particularly limited, for example including any of the variety of cleaning compositions described below. In an embodiment, the traced material in the films 10, 20 is a bitterant or other aversive, and the composition 50 is a detergent or other non-edible composition (e.g., laundry or dishwashing detergent), in particular when the composition 50 is colored or otherwise attractive to children and/or poses health hazards if ingested by a person or animal.

The water-soluble polymer composition can be formed by mixing a tracer composition according to any of the variously disclosed embodiments with a water-soluble polymer and optionally one or more other polymer composition components (e.g., an additional polymer, a plasticizer, another additive) to form polymer-fluorophore-traced material blend. The blend is then formed into a solid water-soluble polymer composition in which the fluorophore and the traced material are substantially homogeneously distributed throughout the water-soluble polymer composition (e.g., resulting from their homogenous distribution in the original tracer composition and the intermediate blend). In one refinement, the polymer-fluorophore-tracer material blend is in the form of an aqueous solution with the water-soluble polymer dissolved therein. In this case, the aqueous solution blend can then be solution cast according to known techniques to form the polymer composition as a film. In another refinement, the polymer composition can be formed by melt processing the polymer-fluorophore-tracer material blend (e.g., injection molding, extrusion, etc. of the blend to form a non-film composition). For example, an aqueous or other liquid-based tracer composition can be added to and dry-mixed with the water-soluble polymer (e.g., in powder or pellet form) and other plasticizers and polymer composition additives to form a dry blend. In another embodiment, a tracer composition which is a homogeneous mixture of fluorophore solids and traced material solids (e.g., in powder form) premixed at a fixed, known ratio similarly can be added to and dry-mixed with the water-soluble polymer components to form a dry blend. In either case, the dry blend can be melt processed according to known techniques to form the water-soluble composition with the fluorophore and traced material.

The disclosure also relates to methods for detecting the fluorophore (and, correspondingly, the traced material) in any of the variously disclosed embodiments for the water-soluble polymer composition (e.g., water-soluble film or otherwise) and the articles made therefrom (e.g., water-soluble pouches or other containers). The composition or article is exposed to incident electromagnetic radiation encompassing one or more characteristic excitation wavelength(s) for the fluorophore, and then emitted electromagnetic radiation from the composition or article is detected at one or more wavelengths corresponding the one or more characteristic excitation wavelength(s) of the fluorophore. The excitation and emission wavelengths can be in the ultraviolet-visible-infrared light spectrum, for instance where the excitation wavelength is in the ultraviolet light spectrum and the emission wavelength is in the visible light spectrum. Positive detection of the fluorophore (e.g., based on positive detection of its characteristic emission wavelength(s)) indicates that the traced material is present in the tested composition or article. Suitably, when the fluorophore and the traced material are present in the composition or article in a known, predetermined ratio, the method can further include quantitatively determining the amount of the fluorophore (e.g., based on a separately generated calibration curve for the fluorophore) and the traced material (e.g., based on the fluorophore result and the predetermined ratio) present in the composition or article.

In a refinement of the general detection method, the composition or article to be tested (or a portion or sample thereof) is an aqueous water-soluble polymer dissolved composition. The dissolved composition can be formed by dissolving an already formed solid water-soluble polymer composition (e.g., as a formed film) in water. Alternatively, the dissolved composition can represent an aqueous solution prior to formation of a solid water-soluble polymer composition (e.g., an aqueous casting solution to which the tracer composition has been added). The dissolved composition in either form is then exposed to the incident electromagnetic radiation encompassing the characteristic excitation wavelength(s) for the fluorophore to generate, detect, and measure the emitted electromagnetic radiation. The dissolved composition can be formed or diluted to any desired level (e.g., expressed as a weight percent of the total water-soluble polymer composition components in water). In any particular case, the concentration of the dissolved composition should be low enough to promote rapid dissolution of the water-soluble polymer composition and avoid fluorescent quenching effects. Similarly, the concentration should be high enough to yield a substantial fluorescent response for the fluorophore. Suitable concentrations for the dissolved composition, in particular for those including polyvinyl alcohol, range from about 0.1 wt. %, 1 wt. %, or 2 wt. % to about 3 wt. %, 5 wt. %, or 10 wt. %.

In another refinement of the general detection method, the method can further include performing a quality control assessment on the composition or article and then taking appropriate (corrective) action as needed. For example, the qualitative or quantitative result for the traced material can be compared to one or more quality control criteria for the traced material (e.g., the traced material must be present, must be present at or above a minimum amount, must be present in prescribed range of amounts, and/or may not be present above a maximum amount). If the composition or article satisfies the quality control criteria, the composition or article (or a batch of compositions or articles corresponding thereto) is accepted; otherwise the composition, article, or related batch is rejected. Rejection of a sample or batch can include destroying, reprocessing, or recycling of the same, or otherwise not using it in the same manner as an accepted item (e.g., keeping it out of the stream of commerce). Acceptance of a sample or batch can include further processing of the same (e.g., forming a sampled film composition into a pouch and filling with a cleaning composition), or allowing a finished product (e.g., filled pouch) to enter stream of commerce.

A variety of means for inducing and detecting a fluorescent response are known in the art. Commercially available spectrophotometers include suitable excitation sources (e.g., ultraviolet LEDs or gas discharge lamps) and detectors that can rapidly and quantitatively detect a sample's fluorescent response (e.g., emitted visible light from a sample cuvette). In an embodiment, the presence of the fluorophore can be screened qualitatively in the water-soluble polymer composition as provided (e.g., in a solid form such as film, without the need to form an aqueous dissolved composition form the same) by exposing the composition to an excitation source (e.g., an ultraviolet gas discharge lamp) and then visually observing the emitted electromagnetic radiation with the human eye (i.e., when the emitted fluorescent wavelength is in the visible spectrum). In other embodiments, there is no naturally visible color to the fluorophore or film, based either on the particular fluorophore used and/or a relatively level of fluorophore incorporation in the film.

The disclosed tracer composition, water-soluble polymer composition, related articles, and related methods are contemplated to include embodiments including any combination of one or more of the additional optional elements, features, and steps further described below (including those shown in the figures and examples), unless stated otherwise.

In any embodiment, the water-soluble polymer composition in the form of a container (e.g., pouch) can include a composition therein. The composition can be selected from a liquid, solid or combination thereof. As used herein, "liquid" includes free-flowing liquids, as well as pastes, gels, foams and mousses. Non-limiting examples of liquids include light duty and heavy duty liquid detergent compositions, fabric enhancers, detergent gels commonly used for laundry, bleach and laundry additives. Gases, e.g., suspended bubbles, or solids, e.g. particles, may be included within the liquids. A "solid" as used herein includes, but is not limited to, powders, agglomerates, and mixtures thereof. Non-limiting examples of solids include: granules, micro-capsules, beads, noodles, and pearlised balls. Solid compositions may provide a technical benefit including, but not limited to, through-the-wash benefits, pre-treatment benefits, and/or aesthetic effects.

In any of the laundry-centric embodiments, the composition may be selected from the group of liquid light duty and liquid heavy duty liquid detergent compositions, powdered detergent compositions, fabric enhancers, detergent gels commonly used for laundry, and bleach (e.g., organic or inorganic bleach) and laundry additives, for example.

As used herein, the term "homopolymer" generally includes polymers having a single type of monomeric repeating unit (e.g., a polymeric chain consisting of or consisting essentially of a single monomeric repeating unit). For the particular case of PVOH, the term "homopolymer" (or "PVOH homopolymer") further includes copolymers having a distribution of vinyl alcohol monomer units and vinyl acetate monomer units, depending on the degree of hydrolysis (e.g., a polymeric chain consisting of or consisting essentially of vinyl alcohol and vinyl acetate monomer units). In the limiting case of 100% hydrolysis, a PVOH homopolymer can include a true homopolymer having only vinyl alcohol units.

As used herein, the term "copolymer" generally includes polymers having two or more types of monomeric repeating units (e.g., a polymeric chain consisting of or consisting essentially of two or more different monomeric repeating units, whether as random copolymers, block copolymers, etc.). For the particular case of PVOH, the term "copolymer" (or "PVOH copolymer") further includes copolymers having a distribution of vinyl alcohol monomer units and vinyl acetate monomer units, depending on the degree of hydrolysis, as well as at least one other type of monomeric repeating unit (e.g., a ter- (or higher) polymeric chain consisting of or consisting essentially of vinyl alcohol monomer units, vinyl acetate monomer units, and one or more other monomer units). In the limiting case of 100% hydrolysis, a PVOH copolymer can include a copolymer having vinyl alcohol units and one or more other monomer units, but no vinyl acetate units.

As used herein, the term "comprising" indicates the potential inclusion of other agents, elements, steps, or features, in addition to those specified.

As used herein and unless specified otherwise, the terms "wt. %" and "wt %" are intended to refer to the composition of the identified element in "dry" (non water) parts by weight of the entire film (when applicable) or parts by weight of the entire composition enclosed within a pouch (when applicable). As used herein and unless specified otherwise, the term "phr" is intended to refer to the composition of the identified element in parts per one hundred parts water-soluble polymer (or resin; whether PVOH or otherwise) in the water-soluble film.

All ranges set forth herein include all possible subsets of ranges and any combinations of such subset ranges. By default, ranges are inclusive of the stated endpoints, unless stated otherwise. Where a range of values is provided, it is understood that each intervening value between the upper and lower limit of that range and any other stated or intervening value in that stated range, is encompassed within the disclosure. The upper and lower limits of these smaller ranges may independently be included in the smaller ranges, and are also encompassed within the disclosure, subject to any specifically excluded limit in the stated range. Where the stated range includes one or both of the limits, ranges excluding either or both of those included limits are also contemplated to be part of the disclosure.

Tracer Composition

As noted above, a tracer composition according to the disclosure is in the form of a homogeneous mixture which includes a fluorophore and a traced material homogeneously distributed throughout the mixture (e.g., in a liquid medium such as water and/or a water-miscible solvent). The fluorophore and the traced material have distinct fluorescence emission spectra to facilitate fluorescent detection of the fluorophore and correlation of the same with detection of the traced material.

A fluorophore is a material that absorbs electromagnetic radiation at one or more characteristic excitation wavelengths and then emits electromagnetic radiation at one or more characteristic emission wavelengths. The emission wavelength can be greater than the excitation wavelength. The electromagnetic radiation for excitation and emission can be in the ultraviolet-visible-infrared light spectrum (e.g., broadly about 10 nm to about 390 nm or about 400 nm for UV light, about 390 nm or about 400 nm to about 700 nm or about 750 nm for visible light, about 700 nm or about 750 nm to about 1 mm for IR light). Fluorophores can be excitable in the UV spectrum (e.g., about 100 nm to about 280 nm (UV-C), about 280 nm to about 315 nm (UV-B), or about 315 nm to about 400 nm (UV-A)) and emit in the visible spectrum (e.g., about 400 nm to about 500 nm, about 500 nm to about 600 nm, or about 600 nm to about 700 nm).

In some aspects, the fluorophore is an organic fluorophore, which typically contains multiple aromatic groups and/or or plane or cyclic groups with multiple pi-bonds. Examples of suitable organic fluorophores include acridines, arylmethines, biphenyl stilbenes, benzoxazolines, coumarins, cyanines, diazoles, fluorones, imidazolines, naphthalenes, oxadiazoles, oxazines, phenanthridines, pyrenes, rhodamines, stilbenes, styryl biphenyls, tetrapyrroles, triazoles, xanthenes, and fluorescent proteins. As understood by the skilled artisan, the suitable fluorophores include various derivatives or analogs of the foregoing, for example including additional organic or inorganic substituents to the base fluorescent molecule.

Optical brighteners (or fluorescent whitening agents) are a class of fluorophores that are commonly used in laundry detergents to provide a whitening effect based on their fluorescent absorption in the UV range (about 340 nm to about 370 nm) and emission in the blue visible range (about 420 nm to about 470 nm). In some aspects, the fluorophore of the tracer composition can be an optical brightener. In a refinement, the same optical brightener fluorophore can be included in both the tracer composition and a detergent composition contained in a pouch or other article formed from the water-soluble polymer composition. In such a case, the use of the same fluorophore in both compositions can have the benefit of providing a supplemental optical brightening effect for laundered articles (e.g., from the tracer composition fluorophore released from the polymer composition upon dissolution while washing) and/or eliminating the addition of a new chemical that might undesirably remain on laundered articles. In another refinement, the tracer composition and detergent fluorophores are different (e.g., the tracer composition fluorophore is not an optical brightener). Such a refinement ensures that possible fluorophores in the detergent do not interfere with detection and/or quantitation of the fluorophore incorporated into the polymer composition (e.g., where a film fluorophore is detected as-is in a detergent pouch with a UV lamp (or "black light") or where the film is sampled/dissolved in water (i.e., and there is a possibility that detergent components may have leached into the film)). In another refinement, a detergent can be substantially free from optical brighteners and/or components with fluorescence emission spectra interfering with (e.g. unduly overlapping with) the tracer composition fluorophore.

Organic fluorophores are generally water-insoluble in their unmodified form. In some aspects, water-soluble organic fluorophore analogs (e.g., having the same or similar base chemical structure and fluorescent activity but including one or more ionic functional groups such as anionic carboxylate, sulfonate, or phosphonate groups, typically in salt form, which impart water solubility) can be used when the traced material and/or the other components of the polymer composition form a compatible mixture with the water-soluble fluorophore analog. In some cases, however, such water-soluble fluorophore analogs would form an incompatible mixture when combined with the traced material and/or the other components of the polymer composition (e.g., a cationic water-soluble component such as a denatonium bitterant in combination with an anionic water-soluble fluorophore analog). Two materials can be said to form an incompatible mixture when they are unable to remain homogeneously distributed in an (aqueous) medium together, such as by phase separation, by reacting to form an insoluble reaction product and/or a product with different chemical properties of the fluorophore or traced material, etc. In such cases, a water-insoluble fluorophore (e.g., without ionic functional groups) can be used to promote homogeneous mixture compatibility and stability.

In other aspects, the fluorophore is an inorganic fluorophore such as a quantum dot. Quantum dots are nanocrystals made of semiconductor materials, and they able to absorb and emit light similarly to organic fluorophores, with a difference being that the emission wavelength is a tunable function of nanocrystal size. Suitable quantum dot materials include cadmium selenide, cadmium sulfide, indium arsenide, and indium phosphide.

In an aspect, the traced material includes an aversive material such as a bitterant material or a pungent material to deter or prevent ingestion of a polymer composition incorporating the aversive material, e.g. by a child or animal. The bitterant adds a bitter taste to the composition to which it is added. Suitable bitterants include denatonium salts (e.g., denatonium benzoate, denatonium saccharide, denatonium chloride), sucrose octaacetate, quinine, flavonoids (e.g., quercetin, naringen), and quassinoids (e.g., quassin, brucine). The pungent adds a sharp biting taste when ingested and a burning sensation when topically applied to and skin. Suitable pungents include capsaicin, piperine, allyl isothiocyanate, and resinferatoxin. Suitable levels of incorporation vary according to the particular bitterant or pungent material. As understood by the skilled artisan, the aversive component should be incorporated as a level sufficiently high to impart the unpleasant taste or sensation, yet sufficiently low to avoid potential toxicity from the aversive itself. Denatonium benzoate is particularly suitable in this regard, as its bitterness threshold is substantially lower than its toxicity threshold.

In another aspect, the traced material includes one or more components of a water-soluble polymer composition. As described in detail below, examples of such traced materials include one or more of water-soluble polymers, plasticizers, plasticizer compatibilizers, lubricants, release agents, fillers, extenders, cross-linking agents, antiblocking agents, antioxidants, detackifying agents, antifoams, nanoparticles, bleaching agents, and surfactants.

Water-insoluble materials in the tracer composition, whether the fluorophore, the traced material, or both, can be homogeneously dispersed throughout the composition as an emulsion, for example using any of a variety of emulsifiers known in the art for stabilization of hydrophobic organic compounds in a hydrophilic medium (e.g., water or a water-containing medium), for example including surfactants and/or detergents. In addition to the various surfactants and detergents described below for inclusion in a water-soluble polymer or a cleaning composition, a suitable class of non-ionic emulsifiers includes polyalkylene oxide-alkyl alcohol ethers (e.g., PEG-4-lauryl alcohol), for example those represented by the formula $R_1(OC_2H_4)_nOH$, wherein $R_1$ is a $C_{10}$-$C_{16}$ alkyl group or a $C_8$-$C_{12}$ alkyl phenyl group, and n is from 3, 4, or 5 to 6, 10, 20, 40, or 80.

The tracer composition can include water and/or a water-miscible solvent to provide a liquid medium for the homogenous mixture of the fluorophore and the traced material in the tracer composition. The water and/or water-miscible solvent provides a liquid medium for a chemically and physically compatible mixture of the fluorophore and traced material. In an aspect, the liquid medium contains at least some water and the homogeneous mixture is an aqueous mixture (e.g., where "aqueous" reflects a water-miscible mixture with a water content of at least 10 wt. %, 25 wt. %, 50 wt. %, 75 wt. %, 90 wt. %, or 95 wt. %, even if water is not the most abundant liquid medium component). The water-miscible solvent, whether used alone or in combination with water, is not particularly limited and can include common polar organic solvents. Examples include alkyl alcohols (e.g., $C_1$-$C_4$ alcohols such as methanol, ethanol, propanol, butanol, and isomers thereof) as well as any of the various hydroxylated plasticizers noted below for the water-soluble polymer compositions. In the event that the liquid medium does not contain added water or includes an additional water-miscible solvent, the fluorophore and the traced material as incorporated into the tracer composition desirably are still compatible and able to form a stable, homogeneous mixture in a liquid medium substantially composed of water (e.g., at least 90 wt. %, 95 wt. %, or 99 wt. % water). Such a property is beneficial when a water-soluble polymer composition including the fluorophore and traced material is dissolved in water, and the resulting aqueous solution is analyzed for the fluorophore. Whatever the selected liquid medium, it desirably is transparent to electromagnetic radiation at the relevant excitation and emission wavelengths of fluorophore (e.g., UV excitation light should be able to penetrate the liquid medium to excite the fluorophore distributed throughout the entire medium; similarly, visible fluorescent emission light should escape the liquid for visual or other optical detection).

The concentrations of the various components of the tracer composition are not particularly limited, and they can be independently selected within broad ranges based on their desired level of incorporation in an eventual water-soluble polymer composition and the relative ratio with which the tracer composition and the water-soluble polymer composition are combined. For instance, the fluorophore (or each fluorophore independently) may be present in the tracer composition at a concentration in a range of about 1 ppm to about 50000 ppm based on weight, for example at least about 1 ppm, 10 ppm, 100 ppm, 1000 ppm, or 10000 ppm and/or up to about 5 ppm, 50 ppm, 500 ppm, 5000 ppm, or 50000 ppm. The traced material (or each traced material independently; e.g., one or more bitterants) may be present in the tracer composition at a concentration in a range of about 10 ppm to about 500000 ppm based on weight, for example at least about 10 ppm, 100 ppm, 1000 ppm, 10000 ppm, 100000 ppm, or 200000 ppm and/or up to about 50 ppm, 500 ppm, 5000 ppm, 50000 ppm, 300000 ppm, or 500000 ppm. The emulsifier (or each emulsifier independently), when included may be present in the tracer composition at a concentration in a range of about 1 ppm to about 50000 ppm based on weight, for example at least about 1 ppm, 10 ppm, 100 ppm, 1000 ppm, or 10000 ppm and/or up to about 5 ppm, 50 ppm, 500 ppm, 5000 ppm, or 50000 ppm. Alternatively or additionally, the emulsifier content may be expressed relative to the concentration of the water-insoluble material it stabilizes, for example at least about 10%, 20%, 50%, or 80% and/or up to about 150%, 200%, 300%, or 500% of the water-insoluble material concentration. The water and/or water-miscible solvent(s) providing the liquid medium of the tracer composition may be at least 10 wt. %, 20 wt. %, 40 wt. %, 60 wt. %, 80 wt. %, 90 wt. %, or 95 wt. % and/or up to 50 wt. %, 70 wt. %, 90 wt. %, or 95 wt. % of the tracer composition.

In an aspect, in addition or as an alternative to particular absolute concentrations, the fluorophore and the traced material can be incorporated into the tracer composition in a known, predetermined ratio. As described above, selection of a predetermined ratio in the tracer composition corresponds to the same ratio in the eventual water-soluble polymer composition and aqueous dilutions thereof, thus permitting quantitative detection of the fluorophore to be correlated to a corresponding quantitative determination of the traced material in the polymer composition. For instance, the predetermined ratio of the fluorophore to the traced material can be in a range of about 0.000001 to 1 by weight, for example at least about 0.000001, 0.00001, 0.0001, 0.001, 0.01, or 0.1 and/or up to about 0.00001, 0.0001, 0.001, 0.01, 0.1, or 1 (e.g., where a ratio of 0.1 indicates, for example, that the fluorophore concentration is 10 wt. % of the traced material concentration).

The tracer composition and/or the resulting water-soluble polymer composition formed therefrom can include a single fluorophore and a single traced material corresponding to the fluorophore. In various refinements, however, the tracer composition and/or the water-soluble polymer composition can include multiple fluorophores, multiple traced materials, or both. For example, a single fluorophore can serve as a marker for multiple traced materials in the tracer composition (e.g., where each traced material has a fluorescence emission spectrum which is distinct from that of the fluorophore when exposed to the characteristic excitation electromagnetic radiation for the fluorophore). When the fluorophore is present in a known ratio with respect to each traced material (e.g., where the known ratio can be the same or different for each traced material relative to the fluorophore), it allows qualitative and/or quantitative identification of each traced material by association with the single fluorophore (e.g., in the eventual water-soluble polymer composition). Alternatively or additionally, the tracer composition and/or the water-soluble polymer composition can include multiple different fluorophores (e.g., where each fluorophore has a fluorescence emission spectrum which is distinct from the other fluorophore emission spectra when exposed to its characteristic excitation electromagnetic radiation). Different fluorophores with distinct emission spectra can result from the use of different chemical species with different spectra or the use of the same chemical species with emission spectra dependent upon some other property of the materials (e.g., particle size for quantum dots). Suitably, all fluorophores are excitable with the same wavelength to provide distinct emission spectra, although multiple excitation wavelengths can be used as needed for different fluorophores. Multiple different fluorophores can be included in the tracer composition and/or the water-soluble polymer composition to provide an independent marker for the multiple traced materials to which each corresponds. In an embodiment, the multiple fluorophores and the multiple traced materials can be included in a single tracer composition for incorporation into the water-soluble polymer composition. In another embodiment, the multiple fluorophores and the multiple traced materials can be into the water-soluble polymer composition using a plurality of different tracer compositions, each including at least one fluorophore and at least one traced material (e.g., two or more of a first tracer composition including a first fluorophore and a traced aversive material, a second tracer composition including a second fluorophore and a traced water-soluble polymer material, a third tracer composition including a third fluorophore and a traced plasticizer material, a fourth tracer composition including a fourth fluorophore and a traced additive material, and combinations thereof). When multiple fluorophores are present each in a known ratio with a corresponding traced material, independent qualitative and/or quantitative identification of each traced material is possible by association with its corresponding fluorophore.

Water-Soluble Polymer Compositions

Water-soluble polymer compositions, optional ingredients for use therein, and methods of making the same are well known in the art (e.g., solvent casting, melt processing such as injection molding or extrusion), whether being used for making relatively thin water-soluble films as already known (e.g., as pouch materials) or relatively thick water-soluble films forming other container structures (e.g. capsules).

As noted above, a water-soluble polymer composition according to the disclosure is in the form of a solid mixture (e.g., a film, pouch, or other form or article) which includes, among other common ingredients described below, a fluorophore and a traced material homogeneously distributed throughout the mixture. The fluorophore and the traced material have distinct fluorescence emission spectra.

The concentrations of the fluorophore and the traced material in the water-soluble polymer composition are not particularly limited, and they can be independently selected within broad ranges based on the desired role of the components in the polymer composition. The fluorophore is incorporated qualitatively at a level which permits it detection by fluorescent emission (e.g., visual inspection by a human, or automated optical detection such as by a spectrophotometer). Similarly, the fluorophore concentration can be selected based on whether it is to be detected as-is in the polymer composition and/or to be detected after dissolution in water at a particular level to form the dissolved polymer composition. For instance, the fluorophore may be present in the water-soluble polymer composition at a concentration in a range of about 1 ppm to about 500 ppm based on weight, for example at least about 1 ppm, 5 ppm, 10 ppm, 20 ppm, or 50 ppm and/or up to about 5 ppm, 10 ppm, 20 ppm, 50 ppm, 100 ppm, or 500 ppm. The traced material concentration is selected based on its intended function in the polymer composition. For instance, an aversive traced material (e.g., bitterant, pungent) may be present in the water-soluble polymer composition at a concentration in a range of about 10 ppm to about 10000 ppm based on weight, for example at least about 10 ppm, 50 ppm, 100 ppm, 200 ppm, 500 ppm, or 1000 ppm and/or up to about 50 ppm, 100 ppm, 500 ppm, 1000 ppm, 5000 ppm, or 10000 ppm. The predetermined ratio of the fluorophore to the traced material in the water-soluble polymer composition can be the same as that for tracer composition (e.g., about 0.000001 to 1 and subranges thereof).

One aspect of the disclosure relates to a plurality of water-soluble polymer compositions in which each water-soluble polymer composition (or batch thereof) is different from each other water-soluble polymer composition (or batch thereof) in at least one aspect, yet each water-soluble polymer composition includes the same fluorophore and the same traced material. The water-soluble polymer compositions can be different in any of a variety of ways, for example having different water-soluble polymers (or amounts thereof), different plasticizers (or amounts thereof), different functional additives (or amounts thereof), etc. Nonetheless, each polymer composition includes the same fluorophore and the same traced material, thus permitting the same analytical method to be used to detect and quantify the fluorophore and traced material in different polymer compositions. In a refinement, the fluorophore and the traced material are present in each water-soluble polymer composition in the same predetermined ratio (e.g., as a result of using the same tracer composition to introduce the fluorophore and traced material into the polymer composition).

In one class of embodiments, the water-soluble polymer composition includes polyvinyl alcohol (PVOH), including homopolymers thereof (e.g., including substantially only vinyl alcohol and vinyl acetate monomer units) and copolymers thereof (e.g., including one or more other monomer units in addition to vinyl alcohol and vinyl acetate units). PVOH is a synthetic resin generally prepared by the alcoholysis, usually termed hydrolysis or saponification, of polyvinyl acetate. Fully hydrolyzed PVOH, wherein virtually all the acetate groups have been converted to alcohol groups, is a strongly hydrogen-bonded, highly crystalline polymer which dissolves only in hot water—greater than about 140° F. (60° C.). If a sufficient number of acetate groups are allowed to remain after the hydrolysis of polyvinyl acetate, the PVOH polymer then being known as partially hydrolyzed, it is more weakly hydrogen-bonded and less crystalline and is soluble in cold water—less than about 50° F. (10° C.). An intermediate cold or hot water soluble polymer composition can include, for example, intermediate partially-hydrolyzed PVOH (e.g., with degrees of hydrolysis of about 94% to about 98%), and is readily soluble only in warm water—e.g., rapid dissolution at temperatures of about 40° C. and greater. Both fully and partially hydrolyzed PVOH types are commonly referred to as PVOH homopolymers although the partially hydrolyzed type is technically a vinyl alcohol-vinyl acetate copolymer.

The degree of hydrolysis (DH) of the PVOH included in the water-soluble polymer compositions of the present disclosure can be in a range of about 75% to about 99% (e.g., about 79% to about 92%, about 86.5% to about 89%, or about 88%, such as for cold-water soluble compositions). As the degree of hydrolysis is reduced, a polymer composition made from the resin will have reduced mechanical strength but faster solubility at temperatures below about 20° C. As the degree of hydrolysis increases, a polymer composition made from the polymer will tend to be mechanically stronger and the thermoformability will tend to decrease. The degree of hydrolysis of the PVOH can be chosen such that the water-solubility of the polymer is temperature dependent, and thus the solubility of a polymer composition made from the polymer, any compatibilizer polymer, and additional ingredients is also influenced. In one option the polymer composition is cold water-soluble. A cold water-soluble polymer composition, soluble in water at a temperature of less than 10° C., can include PVOH with a degree of hydrolysis in a range of about 75% to about 90%, or in a range of about 80% to about 90%, or in a range of about 85% to about 90%. In another option the polymer composition is hot water-soluble. A hot water-soluble polymer composition, soluble in water at a temperature of at least about 60° C., can include PVOH with a degree of hydrolysis of at least about 98%.

Other water soluble polymers for use in addition to or in an alternative to PVOH can include, but are not limited to modified polyvinyl alcohols, polyacrylates, water-soluble acrylate copolymers, polyvinyl pyrrolidone, polyethyleneimine, pullulan, water-soluble natural polymers including, but not limited to, guar gum, xanthan gum, carrageenan, and starch, water-soluble polymer derivatives including, but not limited to, ethoxylated starch and hydroxypropylated starch, copolymers of the forgoing and combinations of any of the foregoing. Yet other water-soluble polymers can include polyalkylene oxides, polyacrylamides, polyacrylic acids and salts thereof, celluloses, cellulose ethers, cellulose esters, cellulose amides, polyvinyl acetates, polycarboxylic acids and salts thereof, polyaminoacids, polyamides, gelatines, methylcelluloses, carboxymethylcelluloses and salts thereof, dextrins, ethylcelluloses, hydroxyethyl celluloses, hydroxypropyl methylcelluloses, maltodextrins, and polymethacrylates. Such water-soluble polymers, whether PVOH or otherwise are commercially available from a variety of sources. Any of the foregoing water-soluble polymers are generally suitable for use as film-forming polymers. Water-soluble polymers particularly suitable for thermal or melt processing into other forms include polyvinyl alcohols, polyethyleneimines, polyvinyl pyrrolidones, polyalkylene oxides, polyacrylamides, cellulose ethers, cellulose esters, cellulose amides, polyvinyl acetates, polyamides, gelatines, methylcelluloses, carboxymethylcelluloses and salts thereof, dextrins, ethylcelluloses, hydroxyethyl celluloses, hydroxypropyl methylcelluloses, maltodextrins, copolymers thereof, blends thereof, and combinations thereof. In general, the water-soluble polymer composition can include copolymers and/or blends of the foregoing resins.

The water-soluble polymers can be included in the polymer composition in an amount in a range of about 30 wt. % or 50 wt. % to about 90 wt. % or 95 wt. %, for example. The weight ratio of the amount of the water-soluble polymer as compared to the combined amount of all plasticizers, compatibilizing agents, and secondary additives can be in a range of about 0.5 to about 18, about 0.5 to about 15, about 0.5 to about 9, about 0.5 to about 5, about 1 to about 3, or about 1 to about 2, for example.

Water-soluble polymers for use in the polymer composition described herein (including, but not limited to PVOH polymers) can be characterized by a viscosity in a range of about 3.0 to about 27.0 cP, about 4.0 cP to about 15 cP, about 4.0 to about 23.0 cP, about 4.0 to about 35.0 cP, about 4.0 to about 40.0 cP, about 6.0 to about 10.0 cP, or about 13.0 to about 27.0 cP. The viscosity of a polymer is determined by measuring a freshly made solution using a Brookfield LV type viscometer with UL adapter as described in British Standard EN ISO 15023-2:2006 Annex E Brookfield Test method. It is international practice to state the viscosity of 4% aqueous polyvinyl alcohol solutions at 20° C. Polymeric viscosities specified herein in cP should be understood to refer to the viscosity of a 4% aqueous water-soluble polymer solution at 20° C., unless specified otherwise.

It is well known in the art that the viscosity of a water-soluble polymer (PVOH or otherwise) is correlated with the weight-average molecular weight ($\overline{M}w$) of the same polymer, and often the viscosity is used as a proxy for $\overline{M}w$. Thus, the weight-average molecular weight of the water-soluble polymer can be in a range of about 30,000 to about 175,000, or about 30,000 to about 100,000, or about 55,000 to about 80,000.

The water-soluble polymer composition can contain other auxiliary agents and processing agents, such as, but not limited to, plasticizers, plasticizer compatibilizers, surfactants, lubricants, release agents, fillers, extenders, cross-linking agents, antiblocking agents, antioxidants, detackifying agents, antifoams, nanoparticles such as layered silicate-type nanoclays (e.g., sodium montmorillonite), bleaching agents (e.g., sodium metabisulfite, sodium bisulfite or others), and other functional ingredients, in amounts suitable for their intended purposes. Embodiments including plasticizers are preferred. The amount of such agents can be up to about 50 wt. %, 20 wt %, 15 wt %, 10 wt %, 5 wt. %, 4 wt % and/or at least 0.01 wt. %, 0.1 wt %, 1 wt %, or 5 wt %, individually or collectively.

The plasticizer can include, but is not limited to, hydroxylated plasticizers such as glycerin, diglycerin, ethylene glycol, diethylene glycol, triethylene glycol, tetraethylene glycol, propylene glycol, polyethylene glycols up to 400 MW, neopentyl glycol, trimethylolpropane, polyether polyols, 2-methyl-1,3-propanediol, lactic acid, ethanolamines, and a mixture thereof. Such plasticizers (e.g., whether in liquid form at room temperature or otherwise) can be included in the water-soluble polymer composition in amounts ranging from about 10 phr or 25 phr to about 30 phr or 50 phr, about 30 phr to about 45 phr, or about 35 phr to about 40 phr, whether for a single plasticizer or a combination of plasticizers. The water-soluble polymer composition can alternatively or additionally include sugar alcohol plasticizers, for example including isomalt, maltitol, sorbitol, xylitol, erythritol, adonitol, dulcitol, pentaerythritol, mannitol and combinations thereof. The sugar alcohol plasticizers can be included in the polymer compositions in amounts ranging from about 5 phr to about 35 phr, about 5 phr to about 25 phr, about 10 phr to about 20 phr, or about 10 phr to about 15 phr, whether for a single sugar alcohol plasticizer or a combination of sugar alcohol plasticizers. The total amount of the plasticizer can be in a range of about 5 wt. % or 10 wt. % to about 30 wt. % or 40 wt. %, or about 15 wt. % to about 35 wt. %, or about 20 wt. % to about 30 wt. %, for example about 25 wt. %.

Suitable surfactants can include the nonionic, cationic, anionic and zwitterionic classes. Suitable surfactants include, but are not limited to, polyoxyethylenated polyoxypropylene glycols, alcohol ethoxylates, alkylphenol ethoxylates, tertiary acetylenic glycols and alkanolamides (nonionics), polyoxyethylenated amines, quaternary ammonium salts and quaternized polyoxyethylenated amines (cationics), and amine oxides, N-alkylbetaines and sulfobetaines (zwitterionics). Other suitable surfactants include dioctyl sodium sulfosuccinate, lactylated fatty acid esters of glycerol and propylene glycol, lactylic esters of fatty acids, sodium alkyl sulfates, polysorbate 20, polysorbate 60, polysorbate 65, polysorbate 80, lecithin, acetylated fatty acid esters of glycerol and propylene glycol, and acetylated esters of fatty acids, and combinations thereof. In various embodiments, the amount of surfactant in the water-soluble polymer composition is in a range of about 0.1 wt % to 2.5 wt %, optionally about 1.0 wt % to 2.0 wt %.

Suitable lubricants/release agents can include, but are not limited to, fatty acids and their salts, fatty alcohols, fatty esters, fatty amines, fatty amine acetates and fatty amides. Preferred lubricants/release agents are fatty acids, fatty acid salts, and fatty amine acetates. In one type of embodiment, the amount of lubricant/release agent in the water-soluble polymer composition is in a range of about 0.02 wt % to about 1.5 wt %, optionally about 0.1 wt % to about 1 wt %.

Suitable fillers/extenders/antiblocking agents/detackifying agents include, but are not limited to, starches, modified starches, crosslinked polyvinylpyrrolidone, crosslinked cellulose, microcrystalline cellulose, silica, metallic oxides, calcium carbonate, talc and mica. Preferred materials are starches, modified starches and silica. In one type of embodiment, the amount of filler/extender/antiblocking agent/detackifying agent in the water-soluble polymer composition is in a range of about 0.1 wt % to about 25 wt %, or about 1 wt % to about 10 wt %, or about 2 wt. % to about 8 wt. %, or about 3 wt. % to about 5 wt. %. In the absence of starch, one preferred range for a suitable filler/extender/antiblocking agent/detackifying agent is about 0.1 wt % or 1 wt % to about 4 wt % or 6 wt %, or about 1 wt. % to about 4 wt. %, or about 1 wt. % to about 2.5 wt. %.

The water-soluble polymer composition can further have a residual moisture content of at least 4 wt. %, for example in a range of about 4 to about 10 wt. %, as measured by Karl Fischer titration.

Other features of water-soluble polymer compositions such as films, including those comprising a capsule shell, may be found in U.S. Publication No. 2011/0189413 and U.S. application Ser. No. 13/740,053, both of which are incorporated by reference herein in their entireties.

Shaping and Sealing

The water-soluble polymer composition can be shaped into a container according to various processes known in the art. For example, a thermally processable water-soluble polymer can be selected and be formed by a melt processing technique (e.g., injection molding) or a thermoforming technique (described below). In a general injection molding process, the water-soluble polymer composition (e.g., including the water-soluble polymer and any additional additives such as plasticizers, etc.) for the capsule shell element is fed into a heated barrel, mixed, and forced into a mold cavity where it cools and hardens to the desired shape defined by the mold. Suitable melt and manifold temperatures for an injection molding process can be in a range of about 200° C. to about 220° C. (e.g., for a suitable melt processable PVOH polymer; temperatures for other water-soluble polymers can be about 10° C. to about 40° C. above the respective polymer's melting point). The barrel tip temperature can be in a range of about 250° C. to about 300° C. (e.g., about 50° C. to about 150° C. above the respective polymer's melting point). The feed section of the barrel is suitably kept cool (e.g., about 40° C.), and a typical temperature for the injection mold is about 60° C. to about 80° C. Other useful thermal processing techniques include compression molding; thermoforming of a cast sheet, fusion deposition (e.g., 3D printing), particle spraying and fusing, and non-melt processes such as sintering (e.g., formation of a solid or porous polymeric shape by heat- (and generally pressure-) induced coalescence of a powdered polymeric material without liquefaction, such as at a temperature below a melting temperature for a crystalline or semi-crystalline polymer). Examples of suitable non-thermal techniques for container or solid composition formation include solvent casting (e.g., using water as the solvent; such as to form a film), coating processes (e.g. spray coating), and machining processes (e.g., machining of capsule shell components from blocks of solid water-soluble polymer).

The water-soluble polymer composition also can be formed as a film and then shaped (e.g., to form a pouch containing the delayed release capsule in addition to other ingredients) according to various processes known in the art, such as by using heat in a thermoforming process. The heat may be applied using any suitable means. For example, the film may be heated directly by passing it under a heating element or through hot air, prior to feeding it onto a surface or once on a surface. Alternatively, it may be heated indirectly, for example by heating the surface or applying a hot item onto the film. The film can be heated using an infrared light. The film may be heated to a temperature in a range of about 50 to about 150° C., about 50 to about 120° C., about 60 to about 130° C., about 70 to about 120° C., or about 60 to about 90° C. Alternatively, the film can be wetted by any suitable means, for example directly by spraying a wetting agent (including water, a solution of the film composition, a plasticizer for the film composition, or any combination of the foregoing) onto the film, prior to feeding it onto the surface or once on the surface, or indirectly by wetting the surface or by applying a wet item onto the film.

Once a film has been heated and/or wetted, it may be drawn into an appropriate mold, preferably using a vacuum. The filling of the molded film with a suitable composition (e.g., a delayed release capsule according to the disclosure, a laundry composition for use in combination therewith, etc.) can be accomplished by utilizing any suitable means. The molded film can be filled by in-line filling techniques, for example. The filled, open packets are then closed forming the pouches, using a second film, by any suitable method. This may be accomplished while in horizontal position and in continuous, constant motion. The closing may be accomplished by continuously feeding a second film, preferably water-soluble film, over and onto the open packets and then preferably sealing the first and second film together, typically in the area between the molds and thus between the packets.

Any suitable method of sealing the packet and/or the individual compartments thereof may be utilized. Non-limiting examples of such means include heat sealing, solvent welding, solvent or wet sealing, and combinations thereof. Typically, only the area which is to form the seal is treated with heat or solvent. The heat or solvent can be applied by any method, typically on the closing material, and typically only on the areas which are to form the seal. If solvent or wet sealing or welding is used, it may be preferred that heat is also applied. Preferred wet or solvent sealing/welding methods include selectively applying solvent onto the area between the molds, or on the closing material, by for example, spraying or printing this onto these areas, and then applying pressure onto these areas, to form the seal. Sealing rolls and belts as described above (optionally also providing heat) can be used, for example.

The formed water-soluble packets or pouches may then be cut by a cutting device. Cutting can be accomplished using any suitable method. It may be preferred that the cutting is also done in continuous manner, and preferably with constant speed and preferably while in horizontal position. The cutting device can, for example, be a sharp item or a hot item, whereby in the latter case, the hot item 'burns' through the film/sealing area in addition to or in the alternative to slicing. The different compartments of multi-compartment pouches may be made together in a side-by-side style wherein the resulting, conjoined pouches may or may not be separated by cutting. Alternatively, the compartments can be made separately. It should be understood that by the use of appropriate feed stations, it may be possible to manufacture multi-compartment pouches incorporating a number of different or distinctive compositions and/or different or distinctive liquid, gel or paste compositions, for example where at least one compartment contains a delayed release capsule according to the disclosure.

Cleaning Compositions

In containers or pouches comprising cleaning or detergent compositions such as laundry, laundry additive, fabric enhancer, and/or dishwashing compositions, the compositions may comprise one or more of the following non-limiting list of ingredients: fabric care benefit agent; detersive enzyme; deposition aid; rheology modifier; builder; inorganic bleach (described above), organic bleach; bleach precursor; bleach booster (or activator); bleach catalyst; perfume and/or perfume microcapsules (see for example U.S. Pat. No. 5,137,646); perfume loaded zeolite; starch encapsulated accord; polyglycerol esters; whitening agent; pearlescent agent; enzyme stabilizing systems; scavenging agents including fixing agents for anionic dyes, complexing agents for anionic surfactants, and mixtures thereof; optical brighteners or fluorescers; polymer including but not limited to soil release polymer and/or soil suspension polymer; dispersants; antifoam agents; non-aqueous solvent; fatty acid; suds suppressors, e.g., silicone suds suppressors (U.S. Publication No. 2003/0060390 A1, ¶ 65-77); cationic starches (US 2004/0204337 A1 and US 2007/0219111 A1); scum dispersants (US 2003/0126282 A1, ¶89-90); dyes; colorants; opacifier; antioxidant; hydrotropes such as toluenesulfonates, cumenesulfonates and naphthalenesulfonates; color speckles; colored beads, spheres or extrudates; clay softening agents. Any one or more of these ingredients is further described in described in European Patent Application Number 09161692.0, U.S. Publication Number 2003/0139312A1, and U.S. Patent Application No. 61/229,981. Additionally or alternatively, the compositions may comprise surfactants and/or solvent systems, each of which is described below.

The detergent compositions can comprise from about 1% to 80% by weight of a surfactant, for example. Detersive surfactants utilized can be of the anionic, nonionic, zwitterionic, ampholytic or cationic type or can comprise compatible mixtures of these types. In one type of embodiment, surfactants are selected from the group consisting of anionic, nonionic, and cationic surfactants, and mixtures thereof. The compositions can be substantially free of betaine surfactants. Examples of detergent surfactants useful herein are described in U.S. Pat. Nos. 3,664,961; 3,919,678; 4,222,905; and 4,239,659. In another type of embodiment surfactants are selected from the group consisting of anionic surfactants, nonionic surfactants, and combinations thereof.

Useful anionic surfactants can themselves be of several different types. For example, water-soluble salts of the higher fatty acids, i.e., "soaps", are useful anionic surfactants in the compositions herein. This includes alkali metal soaps such as the sodium, potassium, ammonium, and alkyl ammonium salts of higher fatty acids containing from about 8 to about 24 carbon atoms, and preferably from about 12 to about 18 carbon atoms. Soaps can be made by direct saponification of fats and oils or by the neutralization of free fatty acids. Particularly useful are the sodium and potassium salts of the mixtures of fatty acids derived from coconut oil and tallow, i.e., sodium or potassium tallow and coconut soap.

Additional non-soap anionic surfactants which are suitable for use herein include the water-soluble salts, preferably the alkali metal, and ammonium salts, of organic sulfuric reaction products having in their molecular structure an alkyl group containing from about 10 to about 20 carbon atoms and a sulfonic acid or sulfuric acid ester group. (Included in the term "alkyl" is the alkyl portion of acyl groups.) Examples of this group of synthetic surfactants include: a) the sodium, potassium and ammonium alkyl sulfates, especially those obtained by sulfating the higher alcohols ($C_8$-$C_{18}$) such as those produced by reducing the glycerides of tallow or coconut oil; b) the sodium, potassium and ammonium alkyl polyethoxylate sulfates, particularly those in which the alkyl group contains from 10 to 22, preferably from 12 to 18 carbon atoms, and wherein the polyethoxylate chain contains from 1 to 15, preferably 1 to 6 ethoxylate moieties; and c) the sodium and potassium alkylbenzene sulfonates in which the alkyl group contains from about 9 to about 15 carbon atoms, in straight chain or branched chain configuration, e.g., those of the type described in U.S. Pat. Nos. 2,220,099 and 2,477,383. Especially valuable are linear straight chain alkylbenzene sulfonates in which the average number of carbon atoms in the alkyl group is from about 11 to 13, abbreviated as $C_{11}$-$C_{13}$ LAS.

Nonionic surfactants can be selected from one or more of those of the formula $R_1(OC_2H_4)_n OH$, wherein $R_1$ is a $C_{10}$-$C_{16}$ alkyl group or a $C_8$-$C_{12}$ alkyl phenyl group, and n is from 3 to about 80. Condensation products of $C_{12}$-$C_{15}$ alcohols with from about 5 to about 20 moles of ethylene oxide per mole of alcohol, e.g., $C_{12}$-$C_{13}$ alcohol condensed with about 6.5 moles of ethylene oxide per mole of alcohol, are specifically contemplated.

The solvent system in the present compositions can be a solvent system containing water alone or mixtures of organic solvents with water. Organic solvents can include 1,2-propanediol, ethanol, glycerol, dipropylene glycol, methyl propane diol and mixtures thereof. Other lower alcohols, $C_1$-$C_4$ alkanolamines such as monoethanolamine and triethanolamine, can also be used. Solvent systems can be absent, for example from anhydrous solid embodiments of the disclosure, but more typically are present at levels in the range of from about 0.1% to about 98%, preferably at least about 1% to about 50%, more usually from about 5% to about 25%.

Organic bleaches can include organic peroxyacids including diacyl and tetraacylperoxides, especially diperoxydodecanedioc acid, diperoxytetradecanedioc acid, and diperoxyhexadecanedioc acid. The organic peroxyacid can be dibenzoyl peroxide. The diacyl peroxide, especially dibenzoyl peroxide, can be present in the form of particles having a weight average diameter of from about 0.1 to about 100 microns, preferably from about 0.5 to about 30 microns, more preferably from about 1 to about 10 microns, for example. In embodiments, at least about 25% to 100%, or at least about 50%, or at least about 75%, or at least about 90%, of the particles are smaller than 10 microns, optionally smaller than 6 microns.

Other organic bleaches include the peroxy acids, particular examples being the alkylperoxy acids and the arylperoxy acids. Representatives include: (a) peroxybenzoic acid and its ring-substituted derivatives, such as alkylperoxybenzoic acids, but also peroxy-α-naphthoic acid and magnesium monoperphthalate; (b) the aliphatic or substituted aliphatic peroxy acids, such as peroxylauric acid, peroxystearic acid, ε-phthalimidoperoxycaproic acid[phthaloiminoperoxyhexanoic acid (PAP)], o-carboxybenzamidoperoxycaproic acid, N-nonenylamidoperadipic acid and N-nonenylamidopersuccinates; and (c) aliphatic and araliphatic peroxydicarboxylic acids, such as 1,12-diperoxycarboxylic acid, 1,9-diperoxyazelaic acid, diperoxysebacic acid, diperoxybrassylic acid, the diperoxyphthalic acids, 2-decyldiperoxybutane-1,4-dioic acid, N,N-terephthaloyldi(6-aminopercaproic acid).

Bleach activators can include organic peracid precursors that enhance the bleaching action in the course of cleaning at temperatures of 60° C. and below. Bleach activators suitable for use herein include compounds which, under perhydrolysis conditions, give aliphatic peroxoycarboxylic acids having preferably from 1 to 10 carbon atoms, in particular from 2 to 4 carbon atoms, and/or optionally substituted perbenzoic acid. Suitable substances bear O-acyl and/or N-acyl groups of the number of carbon atoms specified and/or optionally substituted benzoyl groups. Preference is given to polyacylated alkylenediamines, in particular tetraacetylethylenediamine (TAED), acylated triazine derivatives, in particular 1,5-diacetyl-2,4-dioxohexahydro-1,3,5-triazine (DADHT), acylated glycolurils, in particular tetraacetylglycoluril (TAGU), N-acylimides, in particular N-nonanoylsuccinimide (NOSI), acylated phenolsulfonates, in particular n-nonanoyl- or isononanoyloxybenzenesulfonate (n- or iso-NOBS), carboxylic anhydrides, in particular phthalic anhydride, acylated polyhydric alcohols, in particular triacetin, ethylene glycol diacetate and 2,5-diacetoxy-2,5-dihydrofuran and also triethylacetyl citrate (TEAC). The bleach activator can be stored and/or delivered in combination with and/or separately from its corresponding organic or inorganic bleach (e.g., in the capsule with the inorganic bleach or separate from the inorganic bleach such as in a water-soluble film packet).

Bleach catalysts for use in the detergent composition herein include the manganese triazacyclononane and related complexes (U.S. Pat. No. 4,246,612, U.S. Pat. No. 5,227,084); Co, Cu, Mn and Fe bispyridylamine and related complexes (U.S. Pat. No. 5,114,611); and pentamine acetate cobalt(III) and related complexes (U.S. Pat. No. 4,810,410). Another description of bleach catalysts suitable for use herein can be found in U.S. Pat. No. 6,599,871, incorporated herein by reference. The bleach catalyst can be stored and/or delivered in combination with and/or separately from its corresponding bleach activator and organic or inorganic bleach (e.g., in the capsule with the inorganic bleach or separate from the inorganic bleach such as in a water-soluble film packet).

Builders suitable for use in the detergent composition described herein include water-soluble builders, including citrates, carbonates, silicate and polyphosphates, e.g. sodium tripolyphosphate and sodium tripolyphosphate hexahydrate, potassium tripolyphosphate and mixed sodium and potassium tripolyphosphate salts.

Enzymes suitable for use in the detergent composition described herein include bacterial and fungal cellulases including CAREZYME and CELLUZYME (Novo Nordisk A/S); peroxidases; lipases including AMANO-P (Amano Pharmaceutical Co.), M1 LIPASE and LIPOMAX (Gist-Brocades) and LIPOLASE and LIPOLASE ULTRA (Novo); cutinases; proteases including ESPERASE, ALCALASE, DURAZYM and SAVINASE (Novo) and MAXATASE, MAXACAL, PROPERASE and MAXAPEM (Gist-Brocades); α and β amylases including PURAFECT OX AM (Genencor) and TERMAMYL, BAN, FUNGAMYL, DURAMYL, and NATALASE (Novo); pectinases; and mixtures thereof. Enzymes can be added herein as prills, granulates, or cogranulates at levels typically in the range from about 0.0001% to about 2% pure enzyme by weight of the cleaning composition.

Suds suppressers suitable for use in the detergent composition described herein include nonionic surfactants having a low cloud point. "Cloud point" as used herein, is a well known property of nonionic surfactants which is the result of the surfactant becoming less soluble with increasing temperature, the temperature at which the appearance of a second phase is observable is referred to as the "cloud point." As used herein, a "low cloud point" nonionic surfactant is defined as a nonionic surfactant system ingredient having a cloud point of less than 30° C., preferably less than about 20° C., and even more preferably less than about 10° C., and most preferably less than about 7.5° C. Low cloud point nonionic surfactants can include nonionic alkoxylated surfactants, especially ethoxylates derived from primary alcohol, and polyoxypropylene/polyoxyethylene/polyoxypropylene (PO/EO/PO) reverse block polymers. Also, such low cloud point nonionic surfactants can include, for example, ethoxylated-propoxylated alcohol (e.g., BASF POLY-TERGENT SLF18) and epoxy-capped poly(oxyalkylated) alcohols (e.g., BASF POLY-TERGENT SLF18B series of nonionics, as described, for example, in U.S. Pat. No. 5,576,281).

Other suitable components for use in the detergent composition described herein include cleaning polymers having anti-redeposition, soil release or other detergency properties.

Anti-redeposition polymers for use herein include acrylic acid containing polymers such as SOKALAN PA30, PA20, PA15, PA10 and SOKALAN CP10 (BASF GmbH), ACUSOL 45N, 480N, 460N (Rohm and Haas), acrylic acid/maleic acid copolymers such as SOKALAN CP5 and acrylic/methacrylic copolymers. Soil release polymers for use herein include alkyl and hydroxyalkyl celluloses (U.S. Pat. No. 4,000,093), polyoxyethylenes, polyoxypropylenes and copolymers thereof, and nonionic and anionic polymers based on terephthalate esters of ethylene glycol, propylene glycol and mixtures thereof.

Heavy metal sequestrants and crystal growth inhibitors are also suitable for use in the detergent, for example diethylenetriamine penta(methylene phosphonate), ethylenediamine tetra(methylene phosphonate) hexamethylenediamine tetra(methylene phosphonate), ethylene diphosphonate, hydroxyethylene-1,1-diphosphonate, nitrilotriacetate, ethylenediaminotetracetate, ethylenediamine-N,N'-disuccinate in their salt and free acid forms.

Suitable for use in the detergent composition described herein is also a corrosion inhibitor, for example organic silver coating agents (especially paraffins such as WINOG 70 sold by Wintershall, Salzbergen, Germany), nitrogen-containing corrosion inhibitor compounds (for example benzotriazole and benzimadazole—see GB-A-1137741) and Mn(II) compounds, particularly Mn(II) salts of organic ligands.

Other suitable components for use in the detergent composition herein include enzyme stabilizers, for example calcium ion, boric acid and propylene glycol.

Suitable rinse additives are known in the art. Commercial rinse aids for dishwashing typically are mixtures of low-foaming fatty alcohol polyethylene/polypropylene glycol ethers, solubilizers (for example cumene sulfonate), organic acids (for example citric acid) and solvents (for example ethanol). The function of such rinse aids is to influence the interfacial tension of the water in such a way that it is able to drain from the rinsed surfaces in the form of a thin coherent film, so that no water droplets, streaks, or films are left after the subsequent drying process. European Patent 0 197 434 B1 describes rinse aids which contain mixed ethers as surfactants. Rinse additives such as fabric softeners and the like are also contemplated and suitable for encapsulation in a film according to the disclosure herein.

Specific contemplated aspects of the disclosure are herein described in the following numbered paragraphs.

1. A tracer composition comprising: an aqueous, homogeneous mixture comprising: a water-insoluble fluorophore having a first fluorescence emission spectrum comprising at least one characteristic emission wavelength when exposed to electromagnetic radiation comprising a characteristic excitation wavelength for the fluorophore, the fluorophore being homogeneously dispersed throughout the mixture, and a water-soluble material having a second fluorescence emission spectrum which is distinct from the first fluorescence emission spectrum when exposed to the same electromagnetic radiation comprising the characteristic excitation wavelength for the fluorophore, the water-soluble material being homogeneously mixed in solution throughout the mixture.

2. A tracer composition comprising: a homogeneous mixture comprising: a water-insoluble fluorophore having a first fluorescence emission spectrum comprising at least one characteristic emission wavelength when exposed to electromagnetic radiation comprising a characteristic excitation wavelength for the fluorophore, the fluorophore being homogeneously dispersed throughout the mixture, a water-soluble material having a second fluorescence emission spectrum which is distinct from the first fluorescence emission spectrum when exposed to the same electromagnetic radiation comprising the characteristic excitation wavelength for the fluorophore, the water-soluble material being homogeneously mixed in solution throughout the mixture, and at least one of water and a water-miscible solvent as a medium for the water-insoluble fluorophore and the water-soluble material.

3. The composition of any of the foregoing paragraphs, wherein the water-soluble material and a water-soluble fluorophore analog, if combined in an aqueous medium, would form an incompatible mixture.

4. The composition of any of the foregoing paragraphs, wherein the water-insoluble fluorophore is homogeneously dispersed throughout the mixture as an emulsion.

5. The composition of the foregoing paragraph, wherein the homogeneous mixture further comprises an emulsifier selected from one or more polyalkylene oxide-alkyl alcohol ethers.

6. The composition of any of the foregoing paragraphs, wherein the water-soluble material comprises a bitterant.

7. The composition of the foregoing paragraph, wherein the bitterant is selected from the group consisting of denatonium salts, sucrose octaacetate, quinine, quercetin, naringen, brucine, quassin, and combinations thereof.

8. The composition of the foregoing paragraph, wherein the bitterant comprises a denatonium salt selected from the group consisting of denatonium benzoate, denatonium saccharide, denatonium chloride, and combinations thereof.

9. The composition of the foregoing paragraph, wherein the bitterant comprises denatonium benzoate.

10. The composition of any of the foregoing paragraphs, wherein the water-soluble material is selected from the group consisting of water-soluble polymers, plasticizers, plasticizer compatibilizers, lubricants, release agents, fillers, extenders, cross-linking agents, antiblocking agents, antioxidants, detackifying agents, antifoams, nanoparticles, bleaching agents, surfactants, pungents, and combinations thereof.

11. The composition of any of the foregoing paragraphs, wherein the fluorophore comprises an organic fluorophore.

12. The composition of the foregoing paragraph, wherein the organic fluorophore is selected from the group consisting of acridines, arylmethines, coumarins, cyanines, fluorones, naphthalenes, oxadiazoles, oxazines, phenanthridines, pyrenes, rhodamines, stilbenes, styryl biphenyls, tetrapyrroles, xanthenes, fluorescent proteins, derivatives thereof, and combinations thereof.

13. The composition of any of the foregoing paragraphs, wherein the fluorophore comprises an inorganic fluorophore.

14. The composition of the foregoing paragraph, wherein the inorganic fluorophore comprises a quantum dot.

15. The composition of any of the foregoing paragraphs, wherein the characteristic excitation wavelength is in the ultraviolet light spectrum, and the characteristic emission wavelength is in the visible light spectrum.

16. The composition of any of the foregoing paragraphs, wherein the fluorophore is present in the composition at a concentration in a range of about 1 ppm to about 50000 ppm based on weight.

17. The composition of any of the foregoing paragraphs, wherein the water-soluble material is present in the composition at a concentration in a range of about 10 ppm to about 500000 ppm based on weight.

18. The composition of any of the foregoing paragraphs, wherein the composition comprises a plurality of different water-soluble materials, each water-soluble material having a fluorescence emission spectrum which is distinct from the first fluorescence emission spectrum when exposed to the electromagnetic radiation comprising the characteristic excitation wavelength for the fluorophore.

19. The composition of any of the foregoing paragraphs, wherein the composition comprises a plurality of different fluorophores, each fluorophore having a fluorescence emission spectrum which is distinct from the other fluorophore fluorescence emission spectra when exposed to the electromagnetic radiation comprising the characteristic excitation wavelength for the fluorophore.

20. The composition of any of the foregoing paragraphs, wherein the fluorophore and the water-soluble material are present in the composition in a known, predetermined ratio.

21. The composition of the foregoing paragraph, wherein the predetermined ratio of the fluorophore to the water-soluble material is in a range of about 0.000001 to 1 by weight.

22. A water-soluble polymer composition comprising: a solid mixture comprising: a water-soluble polymer, a fluorophore having a first fluorescence emission spectrum comprising at least one characteristic emission wavelength when exposed to electromagnetic radiation comprising a characteristic excitation wavelength for the fluorophore, the fluorophore being homogeneously distributed throughout the mixture, and a material having a second fluorescence emission spectrum which is distinct from the first fluorescence emission spectrum when exposed to the electromagnetic radiation comprising the characteristic excitation wavelength for the fluorophore, the material being homogeneously distributed throughout the mixture; wherein: when the water-soluble polymer composition is dissolved and mixed in water to form a dissolved composition, the fluorophore remains homogeneously distributed throughout the dissolved composition.

23. The composition of paragraph 22, wherein: the fluorophore is water-insoluble and remains homogeneously dispersed throughout the dissolved composition; and the material is water-soluble and remains homogeneously mixed in solution throughout the dissolved composition.

24. The composition of paragraph 23, wherein the solid mixture further comprises a emulsifier which maintains the fluorophore as a homogeneously dispersed emulsion throughout the dissolved composition.

25. The composition of paragraph 22, wherein: the fluorophore is water-soluble and remains homogeneously mixed in solution throughout the dissolved composition; and the material is water-insoluble and remains homogeneously dispersed throughout the dissolved composition.

26. The composition of paragraph 25, wherein the solid mixture further comprises a emulsifier which maintains the material as a homogeneously dispersed emulsion throughout the dissolved composition.

27. The composition of paragraph 22, wherein the fluorophore and the material are water-soluble and remain homogeneously mixed in solution throughout the dissolved composition.

28. The composition of paragraph 22, wherein the fluorophore and the material are water-insoluble and remain homogeneously dispersed throughout the dissolved composition.

29. The composition of paragraph 28, wherein the solid mixture further comprises at least one emulsifier which maintains the fluorophore and the material as homogeneously dispersed emulsions throughout the dissolved composition.

30. The composition of any one of paragraphs 22 to 29, wherein the water-soluble polymer has a 4% solution viscosity at 20° C. in a range of about 4 cP to about 40 cP.

31. The composition of any one of paragraphs 22 to 30, wherein the water-soluble polymer is selected from the group consisting of polyvinyl alcohols, polyethyleneimines, polyvinyl pyrrolidones, polyalkylene oxides, polyacrylamides, cellulose ethers, cellulose esters, cellulose amides, polyvinyl acetates, polyamides, gelatines, methylcelluloses, carboxymethylcelluloses and salts thereof, dextrins, ethylcelluloses, hydroxyethyl celluloses, hydroxypropyl methylcelluloses, maltodextrins, copolymers thereof, blends thereof, and combinations thereof.

32. The composition of any one of paragraphs 22 to 30, wherein the water-soluble polymer comprises polyvinyl alcohol.

33. The composition of paragraph 32, wherein the polyvinyl alcohol has a degree of hydrolysis in a range of about 75% to about 99%.

34. The composition of paragraph 32, wherein the polyvinyl alcohol comprises a polyvinyl alcohol copolymer consisting essentially of vinyl alcohol monomeric repeat units and vinyl acetate monomeric repeat units.

35. The composition of paragraph 32, wherein the polyvinyl alcohol comprises a polyvinyl alcohol copolymer comprising vinyl alcohol monomeric repeat units, vinyl acetate monomeric repeat units, and at least one other type of monomeric repeat units.

36. The composition of any of paragraphs 22 to 35, wherein the material comprises a bitterant.

37. The composition of paragraph 36, wherein the bitterant is selected from the group consisting of denatonium salts, sucrose octaacetate, quinine, quercetin, naringen, brucine, quassin, and combinations thereof.

38. The composition of paragraph 36, wherein the bitterant comprises a denatonium salt selected from the group consisting of denatonium benzoate, denatonium saccharide, denatonium chloride, and combinations thereof.

39. The composition of paragraph 36, wherein the bitterant comprises denatonium benzoate.

40. The composition of any of paragraphs 22 to 35, wherein the material is selected from the group consisting of additional water-soluble polymers, plasticizers, plasticizer compatibilizers, lubricants, release agents, fillers, extenders, cross-linking agents, antiblocking agents, antioxidants, detackifying agents, antifoams, nanoparticles, bleaching agents, surfactants, pungents, and combinations thereof.

41. The composition of any one of paragraphs 22 to 40, wherein the fluorophore comprises an organic fluorophore.

42. The composition of paragraph 41, wherein the organic fluorophore is selected from the group consisting of acridines, arylmethines, coumarins, cyanines, fluorones, naphthalenes, oxadiazoles, oxazines, phenanthridines, pyrenes, rhodamines, stilbenes, styryl biphenyls, tetrapyrroles, xanthenes, fluorescent proteins, derivatives thereof, and combinations thereof.

43. The composition of any of paragraphs 22 to 40, wherein the fluorophore comprises an inorganic fluorophore.

44. The composition of paragraph 43, wherein the inorganic fluorophore comprises a quantum dot.

45. The composition of any of paragraphs 22 to 44, wherein the characteristic excitation wavelength is in the ultraviolet light spectrum, and the characteristic emission wavelength is in the visible light spectrum.

46. The composition of any one of paragraphs 22 to 45, wherein the fluorophore and the material are present in the composition in a known, predetermined ratio.

47. The composition of paragraph 46, wherein the predetermined ratio of the fluorophore to the material is in a range of about 0.000001 to 1 by weight.

48. The composition of any one of paragraphs 22 to 47, wherein the fluorophore is present in the composition at a concentration in a range of about 1 ppm to about 500 ppm by weight.

49. The composition of any one of paragraphs 22 to 48, wherein the material is present in the composition at a concentration in a range of about 10 ppm to about 10000 ppm by weight.

50. The composition of any one of paragraphs 22 to 49, wherein the water-soluble polymer composition is in the form of a water-soluble film.

51. A plurality of water-soluble polymer compositions comprising: two or more water-soluble polymer compositions of any one of paragraphs 22 to 50, wherein: each water-soluble polymer composition is different from each other water-soluble polymer composition in at least one aspect, and each water-soluble polymer composition comprises the same fluorophore and the same material.

52. The plurality of water-soluble polymer compositions of paragraph 51, wherein the fluorophore and the material are present in each water-soluble polymer composition in the same predetermined ratio.

53. An article comprising: a water-soluble polymer composition of any one of paragraphs 22 to 50 in the form of a container defining an interior container volume; and a composition contained in the interior container volume.

54. The article of paragraph 53, wherein the composition comprises a cleaning composition.

55. The article of paragraph 53, wherein the composition comprises a detergent composition.

56. The article of paragraph 55, wherein the detergent composition comprises the same fluorophore as the water-soluble polymer composition.

57. The article of paragraph 55, wherein the fluorophore comprises an optical brightener.

58. The article of paragraph 55, wherein the detergent composition is substantially free from the fluorophore in the water-soluble polymer composition.

59. The article of any one of paragraphs 53 to 58, wherein: the water-soluble polymer composition is in the form of a water-soluble film, and the container is in the form of a water-soluble pouch.

60. A method for forming a water-soluble polymer composition, the method comprising: mixing a water-soluble polymer and a tracer composition of any one of paragraphs 1 to 21 to form a polymer-fluorophore-material blend; and forming the polymer-fluorophore-material blend into a solid water-soluble polymer composition, wherein the fluorophore and the material are homogeneously distributed throughout the water-soluble polymer composition.

61. A method for forming a water-soluble polymer composition, the method comprising: mixing a water-soluble polymer and a tracer composition to form a polymer-fluorophore-material blend, wherein the tracer composition comprises a homogeneous mixture comprising: a fluorophore having a first fluorescence emission spectrum comprising at least one characteristic emission wavelength when exposed to electromagnetic radiation comprising a characteristic excitation wavelength for the fluorophore, the fluorophore being homogeneously distributed throughout the mixture, and a material having a second fluorescence emission spectrum which is distinct from the first fluorescence emission spectrum when exposed to the electromagnetic radiation comprising the characteristic excitation wavelength for the fluorophore, the material being homogeneously distributed throughout the mixture; and forming the polymer-fluorophore-material blend into a solid water-soluble polymer composition, wherein the fluorophore and the material are homogeneously distributed throughout the water-soluble polymer composition.

62. The method of paragraph 61, wherein the homogeneous mixture further comprises at least one of water and a water-miscible solvent as a medium for the fluorophore and the material.

63. The method of any one of paragraphs 60 to 62, wherein the polymer-fluorophore-material blend further comprises one or more components selected from the group consisting of additional water-soluble polymers, plasticizers, plasticizer compatibilizers, lubricants, release agents, fillers, extenders, cross-linking agents, antiblocking agents, antioxidants, detackifying agents, antifoams, nanoparticles, bleaching agents, surfactants, and combinations thereof.

64. The method of any one of paragraphs 60 to 63, wherein: the polymer-fluorophore-material blend is in the form of an aqueous solution with the water-soluble polymer dissolved therein, and forming the water-soluble polymer composition comprises solution casting the polymer-fluorophore-material blend to form the water-soluble polymer composition as a film.

65. The method of any one of paragraphs 60 to 63, wherein forming the water-soluble polymer composition comprises melt processing the polymer-fluorophore-material blend.

66. A method for detecting a fluorophore, the method comprising: providing a water-soluble polymer composition of any one of paragraphs 22 to 50 or an article of any one of paragraphs 53 to 59; exposing the composition or article to incident electromagnetic radiation comprising the characteristic excitation wavelength for the fluorophore; detecting for emitted electromagnetic radiation from the composition or article, the emitted electromagnetic radiation corresponding to the at least one characteristic emission wavelength of the fluorophore, wherein positive detection of the characteristic emission wavelength indicates that the material is present in the composition or article.

67. The method of paragraph 66, wherein exposing the composition or article to incident electromagnetic radiation comprises: dissolving at least a portion of the water-soluble polymer composition or article in water to form a dissolved composition, and exposing the dissolved composition to the incident electromagnetic radiation comprising the characteristic excitation wavelength for the fluorophore to generate the emitted electromagnetic radiation.

68. The method of paragraph 67, wherein the dissolved composition comprises about 0.1 wt. % to about 10 wt. % of the water-soluble polymer composition or article portion.

69. The method of any one of paragraphs 66 or 68, further comprising: quantitatively determining the amount of the fluorophore present in the composition or article, wherein the fluorophore amount indicates the amount of the material present in the composition or article, when the fluorophore and the material are present in the composition or article in a known, predetermined ratio.

70. The method of any of paragraphs 66 to 69, wherein the at least one excitation wavelength and the at least one emission wavelength are in the ultraviolet-visible-infrared light spectrum.

71. The method of any of paragraphs 66 to 69, wherein: the at least one excitation wavelength is in the ultraviolet light spectrum, and the at least one emission wavelength is in the visible light spectrum.

72. The method of any of paragraphs 66 to 71, comprising detecting the emitted electromagnetic radiation from the sample with a spectrophotometer.

73. The method of any of paragraphs 66 to 72, comprising detecting the emitted electromagnetic radiation from the sample by visual inspection with a human eye when the at least one emission wavelength is in the visible light spectrum.

74. The method of any of paragraphs 66 to 73, further comprising: comparing the qualitative or quantitative determination for the material to one or more quality control criteria for the material, and rejecting or accepting the composition or article based on the comparison.

EXAMPLES

Homogeneous Dissolution Test

A water-soluble polymer composition including a fluorophore tracer (e.g., a film or related article such as a pouch or other container) to be tested for its ability to release the fluorophore and form a dissolved polymer composition with the fluorophore homogeneously distributed throughout the dissolved composition may be tested as follows. A portion of the water-soluble polymer composition is sampled (e.g., a 1 g, 2 g, 5 g, or 10 g sample; alternatively can include an entire article such as a container made from the water-soluble polymer composition) and diluted in water with sufficient water to dissolve the water-soluble polymer component(s) and form the dissolved composition. Suitably, a 1 wt. %, 2 wt. %, 5 wt. %, or 10 wt. % solution of the polymer composition in deionized water is formed. A 2 wt. % solution is suitable for PVOH-based compositions, as it permits timely dissolution of the PVOH polymer component. The dissolved composition is mixed (e.g., with a magnetic stirring rod, shaking, or agitation, etc.) under ambient conditions (e.g., about 20° C. to 25° C.; about 25° C.) for sufficient time to completely dissolve the water-soluble polymer.

Suitable behavior for the water-soluble polymer compositions disclosed herein is marked by a dissolved composition in which the fluorophore originally contained in the polymer composition is homogeneously distributed throughout the dissolved composition. This quality permits quantitative detection of the fluorophore in the dissolved composition and subsequent quantitative determination of the other component(s) in the polymer composition to which the fluorophore corresponds according to a known ratio (e.g., bitterant or otherwise). Homogeneity of the resulting dissolved composition can be evaluated visually: There should be no observable precipitates or separate phases in the dissolved composition (e.g., fluorophore alone, other composition components alone, insoluble reaction products between the fluorophore and other composition components). Visual inspection can be performed with a UV lamp when the fluorophore has a UV excitation wavelength and a visible emission wavelength: Irradiation with the UV lamp should reveal a dissolved composition with a continuous color corresponding to the visible emission wavelength (i.e., absence of visibly concentrated areas of fluorescent material in the dissolved composition). Homogeneity of the resulting dissolved composition also can be evaluated quantitatively: The concentration of the fluorophore in the can be measured (e.g., spectrophotometrically as generally described herein) and compared with a replicate measurement from the dissolved composition and/or with a known theoretical value based on the level of fluorophore incorporation in the polymer composition.

Example 1

Fluorescent Tracer in PVOH Solution

Figure 3:
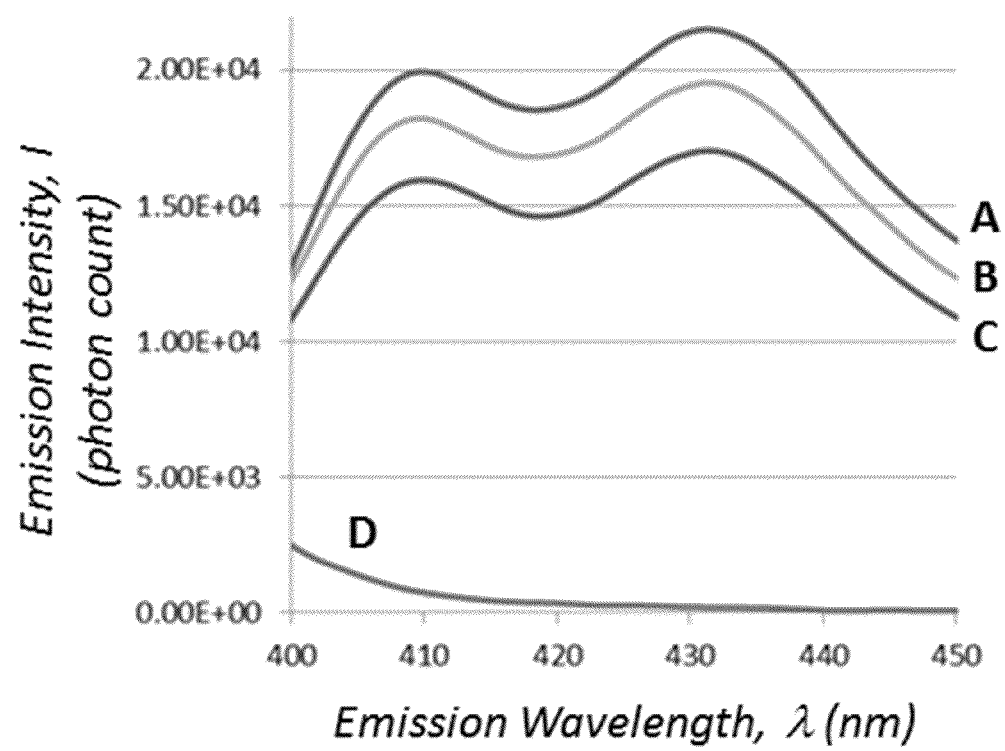
FIG. 3 is graph illustrating the fluorescence emission spectra polyvinyl alcohol solutions with and without fluorophores.

An aqueous tracer composition according to the disclosure was formed by dissolving a water-soluble fluorophore into a 2 wt. % solution of PVOH copolymer film in deionized water. The fluorophore was a water-soluble, disodium disulfonate derivative of distyryl biphenyl commonly used as an optical brightener (or fluorescent whitening agent) in detergent powders (BENETEX OB-M1; available from Mayzo Specialty Chemicals, GA). The fluorophore is excitable with UV light (e.g., at about 340 nm to about 370 nm) and has a characteristic peak visible fluorescence emission at about 440 nm. The fluorophore was dissolved in solutions at levels of 1.8 ppm, 2.0 ppm, and 2.2 ppm. Using a BLACK-COMET spectrometer (available from StellarNet, FL), the solutions with the fluorophore and a control solution with no fluorophore were excited with a 365 nm UV LED and emitted light ranging from 400 nm to 450 nm was measured. As illustrated in FIG. 3, this example shows that the quantitative analysis technique has a high level of sensitivity to fluorescence (i.e., at least on the order of about 1 ppm or less) and was able to quantifiably show differences in fluorescence between samples which differed in fluorophore concentration by just 0.2 ppm (curves A, B, and C in FIG. 3, corresponding to 2.2 ppm, 2.0 ppm, and 1.8 ppm fluorophore, respectively). Further, the example shows that, although the PVOH film has a measurable fluorescence emission spectrum in the range of 400 nm to 450 nm, the fluorescent response is sufficiently small in comparison with that of the fluorophore so that the emission spectra of the fluorophore and the film components are distinct and non-interfering (curve D in FIG. 3, corresponding to 0 ppm fluorophore). Analysis of the results also shows a high level of linearity between the fluorescent emission intensity (photon count) at 440 nm and fluorescence concentration ($r^2$=0.9988; not shown).

As noted previously, this water-soluble distyryl biphenyl fluorophore is not suitable for use as a tracer in combination with a denatonium bitterant film additive because the sulfonated distyryl biphenyl and denatonium bitterant form a water-insoluble salt precipitate, thus preventing homogeneous incorporation of the two components into the film by typical film-forming techniques and/or reliable quantitative or qualitative detection of the fluorophore. This example illustrates, however, that the water-soluble distyryl biphenyl fluorophore is a suitable fluorescent tracer for one or more other film components (e.g., water-soluble polymer resin, plasticizer, other additives), whether water-soluble or water-insoluble, insofar as the fluorophore was found to form a homogeneous, compatible mixture between the fluorophore and the other film components.

Example 2

Fluorescent Tracer and Bitterant

A tracer composition according to the disclosure was formed by combining a water-insoluble fluorophore with a water-soluble bitterant in a homogeneous liquid mixture. A mixture of denatonium benzoate (25 wt. %) as a water-soluble bitterant in propylene glycol (75 wt. %) (BITREX; available from Bitrex, Edinburgh, UK) was combined with 4-methyl-7-(diethylamino) coumarin (OPTIBLANC ATR; available from 3V, Bergamo, Italy) as a water-insoluble fluorophore stabilized as an emulsion in water with tetra(polyethylene glycol)-lauryl alcohol ether (HO—[$C_2H_4O$]$_4$—$C_{12}H_{25}$; "PEG-4-lauryl alcohol ether" or "laureth-4") as an emulsifier. The fluorophore is excitable with UV light (e.g., at about 340 nm to about 370 nm) and has a characteristic peak visible fluorescence emission at about 440 nm. As formed, the fluorophore and the bitterant were present in the tracer composition in a predetermined ratio of 0.07 by weight (i.e., 0.07 wt. parts fluorophore per weight part bitterant). The combination was well mixed to provide a homogeneous mixture of the water-soluble bitterant and the water-insoluble fluorophore. The mixture components were compatible (e.g., no observable settling, precipitation, phase separation), and the mixture was observed to be stable in storage under ambient laboratory condition for a period of at least about a month without any visual indication of instability or inhomogeneity (e.g., no observed phase separation and/or precipitation of fluorophore or other mixture components). Although such tracer compositions are believed to remain stably homogeneous without substantial settling for periods of several months (e.g., at least about 1, 2, 3, or 4 months and/or up to about 3, 6, 9, or 12 months), the tracer composition can be re-mixed or otherwise re-agitated before use (e.g., shortly before combination with a water-soluble polymer to form a water-soluble polymer composition) ensure homogeneity of the tracer composition and incorporation of its components into the water-soluble polymer composition at the intended level. The concentrations of tracer composition components are summarized in Table 1 below.

TABLE 1

Tracer Composition (Example 2)

| Component | Amount |
| --- | --- |
| Denatonium benzoate (bitterant) | 20 wt. % |
| Propylene glycol | 60 wt. % |
| 4-Methyl-7-(diethylamino) coumarin (fluorophore) | 1.4 wt. % |
| PEG-4-lauryl alcohol ether (emulsifier) | 6.0 wt. %-8.6 wt. % |
| Water | 10.0 wt. %-12.6 wt. % |

Examples 3

Fluorescent Tracer and Bitterant in Water-Soluble Film

A water-soluble polymer film composition according to the disclosure was formed including a fluorescent tracer and a bitterant aversive. A control PVOH copolymer film (Film A) was formed by solvent casting from an aqueous casting solution of the film components. The control PVOH copolymer film composition included about 55 wt. % to 70 wt. % of a water-soluble PVOH copolymer (23 cP solution viscosity, 88% degree of hydrolysis), about 25 wt. % to 35 wt. % of water-soluble hydroxylated plasticizers, about 0.5 wt. % to 2 wt. % of minor additives such as lubricants, release agents, fillers, extenders, antiblocking agents, and detackifying agents, and about 5 wt. % to 10 wt. % water. A PVOH copolymer film according to the disclosure (Film B) was formed in the same manner as the control Film A, with the exception that 0.5 weight parts of the tracer composition of Example 2 were added to the casting solution just prior to casting per 100 weight parts of the film components in the casting solution. As a result, Film B additionally contained 1000 ppm (weight basis) of denatonium benzoate bitterant and 70 ppm (weight basis) of 4-methyl-7-(diethylamino) coumarin fluorophore. The concentrations of film components are summarized in Table 2 below.

TABLE 2

Water-Soluble Polymer Films (Example 3)

| Component | Film A | Film B |
| --- | --- | --- |
| PVOH copolymer | 55 wt. % to 70 wt. % | 55 wt. % to 70 wt. % |
| Hydroxylated plasticizer | 25 wt. % to 35 wt. % | 25 wt. % to 35 wt. % |
| Film additives | 0.5 wt. % to 2 wt. % | 0.5 wt. % to 2 wt. % |
| Water | 5 wt. % to 10 wt. % | 5 wt. % to 10 wt. % |
| Denatonium benzoate (bitterant) | — | 0.1 wt. % |
| Propylene glycol | — | 0.3 wt. % |
| 4-Methyl-7-(diethylamino) coumarin (fluorophore) | — | 0.007 wt. % |
| PEG-4-lauryl alcohol ether (emulsifier) | — | 0.03 wt. %-0.043 wt. % |

Figure 4:
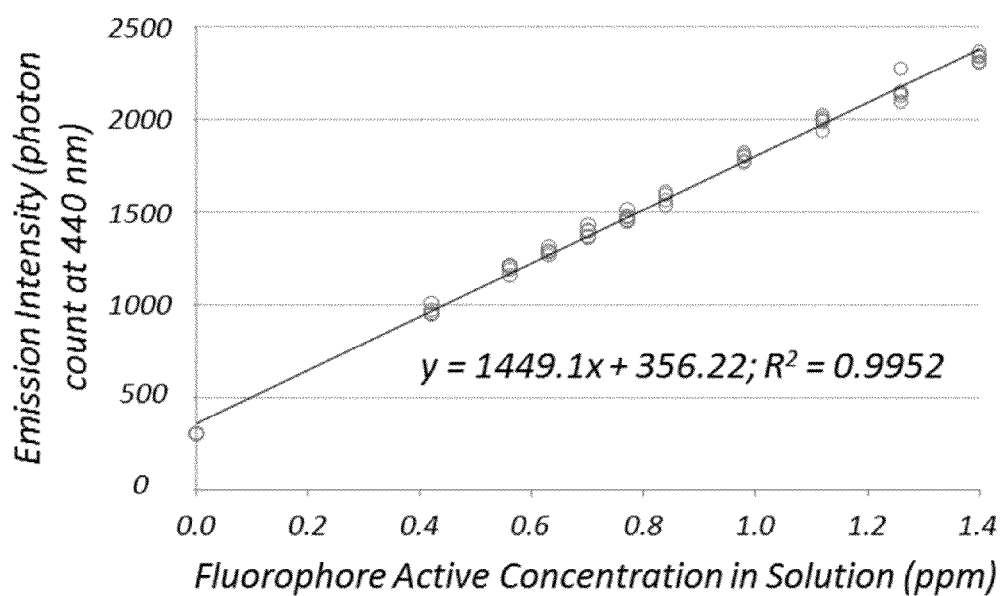
FIG. 4 is a graph illustrating the concentration dependence of fluorescent emission intensity as function of fluorophore concentration incorporated into a polyvinyl alcohol film according to the disclosure.

The two film formulations were used to create serial dilutions for fluorescence testing. 10 g of film was dissolved in deionized water at a 50:1 dilution to create a 2 wt. % solution of each Film A and Film B. These two solutions were then combined in various proportions ranging from 100% Film A solution to 100% Film B solution to produce 25 g solutions of various fluorophore and bitterant concentrations along with the other dissolved film components. In addition a control solution with 0 ppm fluorophore and bitterant, other solutions with 0.42 ppm to 1.4 ppm fluorophore and 6 ppm to 20 ppm bitterant (i.e., each with the 0.07 fluorophore:bitterant ratio) were formed. A 3-ml test sample of each concentration was taken using a micropipette and deposited into a quartz cuvette which was then put into the cuvette sample holder of the BLACK-COMET spectrometer (available from StellarNet, FL). The samples were subjected to UV light (source LED at 365 nm with 275 ms exposure time selected to increase response without detector saturation) in the spectrometer. The samples fluoresced to varying degrees, and the emitted fluorescing light at 440 nm was collected and measured by the spectrometer (FIG. 4). As illustrated in FIG. 4, this example also shows that the quantitative analysis technique has a high level of sensitivity to fluorescence (i.e., at least on the order of about 0.4 ppm or less) and was able to quantifiably show differences in fluorescence between samples which differed in fluorophore concentration by about 0.1 ppm. As illustrated, analysis of the results also shows a high level of linearity between the photon count and fluorescence concentration ($r^2$=0.9952).

The foregoing description is given for clearness of understanding only, and no unnecessary limitations should be understood therefrom, as modifications within the scope of the invention may be apparent to those having ordinary skill in the art.

Throughout this specification and the claims which follow, unless the context requires otherwise, the word "comprise" and variations such as "comprises" and "comprising" will be understood to imply the inclusion of a stated integer or step or group of integers or steps but not the exclusion of any other integer or step or group of integers or steps.

Throughout the specification, where compositions are described as including components or materials, it is contemplated that the compositions can also consist essentially of, or consist of, any combination of the recited components or materials, unless described otherwise. Likewise, where methods are described as including particular steps, it is contemplated that the methods can also consist essentially of, or consist of, any combination of the recited steps, unless described otherwise. The invention illustratively disclosed herein suitably may be practiced in the absence of any element or step which is not specifically disclosed herein.

The practice of a method disclosed herein, and individual steps thereof, can be performed manually and/or with the aid of or automation provided by electronic equipment. Although processes have been described with reference to particular embodiments, a person of ordinary skill in the art will readily appreciate that other ways of performing the acts associated with the methods may be used. For example, the order of various of the steps may be changed without departing from the scope or spirit of the method, unless described otherwise. In addition, some of the individual steps can be combined, omitted, or further subdivided into additional steps.

All patents, publications and references cited herein are hereby fully incorporated by reference. In case of conflict between the present disclosure and incorporated patents, publications and references, the present disclosure should control.

What is claimed:

1. A tracer composition comprising:
    an aqueous, homogeneous mixture comprising:
        a water-insoluble fluorophore having a first fluorescence emission spectrum comprising at least one characteristic emission wavelength when exposed to electromagnetic radiation comprising a characteristic excitation wavelength for the fluorophore, the fluorophore being homogeneously dispersed throughout the mixture, and
        a water-soluble material having a second fluorescence emission spectrum which is distinct from the first fluorescence emission spectrum when exposed to the same electromagnetic radiation comprising the characteristic excitation wavelength for the fluorophore, the water-soluble material being homogeneously mixed in solution throughout the mixture.

2. The composition of claim 1, wherein the water-soluble material and a water-soluble fluorophore analog, if combined in an aqueous medium, would form an incompatible mixture.

3. The composition of claim 1, wherein the water-insoluble fluorophore is homogeneously dispersed throughout the mixture as an emulsion.

4. The composition of claim 3, wherein the homogeneous mixture further comprises an emulsifier selected from one or more polyalkylene oxide-alkyl alcohol ethers.

5. The composition of claim 1, wherein the water-soluble material comprises a bitterant.

6. The composition of claim 5, wherein the bitterant is selected from the group consisting of denatonium salts, sucrose octaacetate, quinine, quercetin, naringen, brucine, quassin, and combinations thereof.

7. The composition of claim 5, wherein the bitterant comprises a denatonium salt selected from the group consisting of denatonium benzoate, denatonium saccharide, denatonium chloride, and combinations thereof.

8. The composition of claim 5, wherein the bitterant comprises denatonium benzoate.

9. The composition of claim 1, wherein the water-soluble material is selected from the group consisting of water-soluble polymers, plasticizers, plasticizer compatibilizers, lubricants, release agents, fillers, extenders, cross-linking agents, antiblocking agents, antioxidants, detackifying agents, antifoams, nanoparticles, bleaching agents, surfactants, pungents, and combinations thereof.

10. The composition of claim 1, wherein the fluorophore comprises an organic fluorophore.

11. The composition of claim 1, wherein the fluorophore comprises an inorganic fluorophore.

12. The composition of claim 1, wherein
    the characteristic excitation wavelength is in the ultraviolet light spectrum, and
    the characteristic emission wavelength is in the visible light spectrum.

13. The composition of claim 1, wherein the composition comprises a plurality of different water-soluble materials, each water-soluble material having a fluorescence emission spectrum which is distinct from the first fluorescence emission spectrum when exposed to the electromagnetic radiation comprising the characteristic excitation wavelength for the fluorophore.

14. The composition of claim 1, wherein the composition comprises a plurality of different fluorophores, each fluorophore having a fluorescence emission spectrum which is distinct from the other fluorophore fluorescence emission spectra when exposed to the electromagnetic radiation comprising the characteristic excitation wavelength for the fluorophore.

15. The composition of claim 1, wherein the fluorophore and the water-soluble material are present in the composition in a known, predetermined ratio.

16. A method for forming a water-soluble polymer composition, the method comprising:
    mixing a water-soluble polymer and a tracer composition of claim 1 to form a polymer-fluorophore-material blend; and
    forming the polymer-fluorophore-material blend into a solid water-soluble polymer composition, wherein the fluorophore and the material are homogeneously distributed throughout the water-soluble polymer composition.

17. A tracer composition comprising:
    a homogeneous mixture comprising:
        a water-insoluble fluorophore having a first fluorescence emission spectrum comprising at least one characteristic emission wavelength when exposed to electromagnetic radiation comprising a characteristic excitation wavelength for the fluorophore, the fluorophore being homogeneously dispersed throughout the mixture,
        a water-soluble material having a second fluorescence emission spectrum which is distinct from the first fluorescence emission spectrum when exposed to the same electromagnetic radiation comprising the characteristic excitation wavelength for the fluorophore, the water-soluble material being homogeneously mixed in solution throughout the mixture, and
        at least one of water and a water-miscible solvent as a medium for the water-insoluble fluorophore and the water-soluble material.

18. A water-soluble polymer composition comprising:
    a solid mixture comprising:
        a water-soluble polymer,
        a fluorophore having a first fluorescence emission spectrum comprising at least one characteristic emission wavelength when exposed to electromagnetic radiation comprising a characteristic excitation wavelength for the fluorophore, the fluorophore being homogeneously distributed throughout the mixture, and
        a material having a second fluorescence emission spectrum which is distinct from the first fluorescence emission spectrum when exposed to the electromagnetic radiation comprising the characteristic excitation wavelength for the fluorophore, the material being homogeneously distributed throughout the mixture;

wherein: when the water-soluble polymer composition is dissolved and mixed in water to form a dissolved composition, the fluorophore remains homogeneously distributed throughout the dissolved composition.

19. The composition of claim 18, wherein:
the fluorophore is water-insoluble and remains homogeneously dispersed throughout the dissolved composition;
the material is water-soluble and remains homogeneously mixed in solution throughout the dissolved composition; and
optionally an emulsifier which maintains the fluorophore as a homogeneously dispersed emulsion throughout the dissolved composition.

20. The composition of claim 18, wherein:
the fluorophore is water-soluble and remains homogeneously mixed in solution throughout the dissolved composition;
the material is water-insoluble and remains homogeneously dispersed throughout the dissolved composition; and
optionally an emulsifier which maintains the material as a homogeneously dispersed emulsion throughout the dissolved composition.

21. The composition of claim 18, wherein the fluorophore and the material are water-soluble and remain homogeneously mixed in solution throughout the dissolved composition.

22. The composition of claim 18, wherein:
the fluorophore and the material are water-insoluble and remain homogeneously dispersed throughout the dissolved composition; and
optionally, the solid mixture further comprises at least one emulsifier which maintains the fluorophore and the material as homogeneously dispersed emulsions throughout the dissolved composition.

23. The composition of claim 18, wherein the water-soluble polymer is selected from the group consisting of polyvinyl alcohols, polyethyleneimines, polyvinyl pyrrolidones, polyalkylene oxides, polyacrylamides, cellulose ethers, cellulose esters, cellulose amides, polyvinyl acetates, polyamides, gelatines, methylcelluloses, carboxymethylcelluloses and salts thereof, dextrins, ethylcelluloses, hydroxyethyl celluloses, hydroxypropyl methylcelluloses, maltodextrins, copolymers thereof, blends thereof, and combinations thereof.

24. The composition of claim 18, wherein the material comprises a bitterant.

25. The composition of claim 18, wherein the fluorophore comprises an organic fluorophore.

26. The composition of claim 18, wherein the water-soluble polymer composition is in the form of a water-soluble film.

27. A plurality of water-soluble polymer compositions comprising:
two or more water-soluble polymer compositions of claim 18, wherein:
each water-soluble polymer composition is different from each other water-soluble polymer composition in at least one aspect, and
each water-soluble polymer composition comprises the same fluorophore and the same material.

28. An article comprising:
a water-soluble polymer composition of claim 18 in the form of a container defining an interior container volume; and
a composition contained in the interior container volume.

29. The article of claim 28, wherein the composition comprises a cleaning composition.

30. The article of claim 28, wherein the composition comprises a detergent composition.

31. The article of claim 30, wherein the detergent composition comprises the same fluorophore as the water-soluble polymer composition.

32. The article of claim 30, wherein the fluorophore comprises an optical brightener.

33. The article of claim 30, wherein the detergent composition is substantially free from the fluorophore in the water-soluble polymer composition.

34. The article of claim 28, wherein:
the water-soluble polymer composition is in the form of a water-soluble film, and
the container is in the form of a water-soluble pouch.

35. A method for detecting a fluorophore, the method comprising:
providing a water-soluble polymer composition of claim 18, or an article comprising the water-soluble polymer composition of claim 18 in the form of a container defining an interior container volume and a composition contained in the interior container volume;
exposing the composition or article to incident electromagnetic radiation comprising the characteristic excitation wavelength for the fluorophore;
detecting for emitted electromagnetic radiation from the composition or article, the emitted electromagnetic radiation corresponding to the at least one characteristic emission wavelength of the fluorophore, wherein positive detection of the characteristic emission wavelength indicates that the material is present in the composition or article.

36. The method of claim 35, comprising detecting the emitted electromagnetic radiation from the sample with a spectrophotometer.

37. The method of claim 35, comprising detecting the emitted electromagnetic radiation from the sample by visual inspection with a human eye when the at least one emission wavelength is in the visible light spectrum.

38. A method for forming a water-soluble polymer composition, the method comprising:
mixing a water-soluble polymer and a tracer composition to form a polymer-fluorophore-material blend, wherein the tracer composition comprises a homogeneous mixture comprising:
a fluorophore having a first fluorescence emission spectrum comprising at least one characteristic emission wavelength when exposed to electromagnetic radiation comprising a characteristic excitation wavelength for the fluorophore, the fluorophore being homogeneously distributed throughout the mixture, and
a material having a second fluorescence emission spectrum which is distinct from the first fluorescence emission spectrum when exposed to the electromagnetic radiation comprising the characteristic excitation wavelength for the fluorophore, the material being homogeneously distributed throughout the mixture; and
forming the polymer-fluorophore-material blend into a solid water-soluble polymer composition, wherein the fluorophore and the material are homogeneously distributed throughout the water-soluble polymer composition.

* * * * *